US006551595B1

(12) United States Patent
Rosengard et al.

(10) Patent No.: US 6,551,595 B1
(45) Date of Patent: Apr. 22, 2003

(54) SMALLPOX INHIBITOR OF COMPLEMENT ENZYMES (SPICE) PROTEIN AND METHODS OF INHIBITING COMPLEMENT ACTIVATION

(75) Inventors: Ariella M. Rosengard, Gladwyne, PA (US); Joseph M. Ahearn, Pittsburgh, PA (US)

(73) Assignees: The Trustees of the University of Pennsylvania; The University of Pittsburgh of the Commonwealth of Pennsylvania

( * ) Notice: Subject to any disclaimer, the term of this patent is extended or adjusted under 35 U.S.C. 154(b) by 12 days.

(21) Appl. No.: 09/653,813

(22) Filed: Sep. 1, 2000

Related U.S. Application Data

(63) Continuation of application No. PCT/US99/04635, filed on Mar. 2, 1999.
(60) Provisional application No. 60/076,821, filed on Mar. 3, 1998.

(51) Int. Cl.[7] .......................... A61K 39/00; C12P 21/06; C12P 21/04; C07H 21/04
(52) U.S. Cl. .................. 424/192.1; 435/69.1; 435/69.7; 536/23.72
(58) Field of Search ............................... 435/69.7, 69.1; 536/23.72; 424/192.1

(56) References Cited

U.S. PATENT DOCUMENTS 5,187,268 A    2/1993    Kotwal et al. ............ 536/23.72

FOREIGN PATENT DOCUMENTS

| WO | WO 91/11461 | 8/1991 |
|---|---|---|
| WO | WO 91/16437 | 10/1991 |
| WO | WO 94/12650 | 6/1994 |
| WO | WO 95/23868 | 9/1995 |
| WO | WO 95/31560 | 11/1995 |
| WO | WO 96/29411 | 9/1996 |

OTHER PUBLICATIONS

Massung et al. (1993) Nature, 366, pp. 748–751.*
Ahearn, et al., 1996, Immunity 4:251–262.
Bird, et al., 1988, Science 242:423–426.
Boulter, et al., 1973, Prog. Med. Virol. 16:86–108.
Croix, et al., 1996, J. Exp. Med. 183:1857–1864.
Finck, et al., 1994, Science 265:1225–1227.
Freed, et al., 1972, Am. J. Med. 52:411–420.
Fulginiti, et al., 1968, Birth Defects 4:129–145.
Hebell, et al., 1991, Science 254:102–105.
Herrera, et al., 1998, J. Virol. 72:294–302.
Huston, et al., 1988, Proc. Natl. Acad. Sci. USA 85:5879–5883.
Karp, et al., 1996, Science 273:228–231.
Kotwal, et al., 1988, Nature (Lond.) 335:176–178.
Kotwal, et al., 1990, Science 250:827–830.
Martin, et al., J. Exp. Med. 1991, 174:1299–1311.
Miller and Rosman, 1992, Biotechniques 7:980–990.
Payne, 1980, J. Gen. Virol. 50:89–100.
Whitelaw, et al., 1992, Biochem J. 286:31–39.

* cited by examiner

Primary Examiner—Tekchand Saidha
(74) Attorney, Agent, or Firm—Licata & Tyrrell P.C.

(57) ABSTRACT

The invention provides a complement inhibitor derived from variola, called smallpox inhibitor of complement enzymes (SPICE) and SPICE-related proteins, such as fusion proteins. These proteins are useful in the treatment of complement-mediated conditions, such as hyperacute rejection of xenografts.

16 Claims, 13 Drawing Sheets

VCP w/T->A at pos 267    -> 1-phase Translation

DNA sequence   789 b.p.   ATGAAGGTGGAG . . . AAATGTGTACGC linear

```
1/1                                    31/11
ATG AAG GTG GAG AGC GTG ACG TTC CTG ACA TTG TTG GGA ATA GGA TGC GTT CTA TCA TGC
Met lys val glu ser val thr phe leu thr leu leu gly ile gly cys val leu ser cys
61/21                                  91/31
TGT ACT ATT CCG TCA CGA CCC ATT AAT ATG AAA TTT AAG AAT AGT GTG GAG ACT GAT GCT
cys thr ile pro ser arg pro ile asn met lys phe lys asn ser val glu thr asp ala
121/41                                 151/51
AAT GCT AAT TAC AAC ATA GGA GAC ACT ATA GAA TAT CTA TGT CTA CCT GGA TAC AGA AAG
asn ala asn tyr asn ile gly asp thr ile glu tyr leu cys leu pro gly tyr arg lys
181/61                                 211/71
CAA AAA ATG GGA CCT ATA TAT GCT AAA TGT ACA GGT ACT GGA TGG ACA CTC TTT AAT CAA
gln lys met gly pro ile tyr ala lys cys thr gly thr gly trp thr leu phe asn gln
241/81                                 271/91
TGT ATT AAA CGG AGA TGC CCA TCG CCA CGA GAT ATC GAT AAT GGC CAA CTT GAT ATT GGT
cys ile lys arg arg cys pro ser pro arg asp ile asp asn gly gln leu asp ile gly
301/101                                331/111
GGA GTA GAC TTT GGC TCT AGT ATA ACG TAC TCT TGT AAT AGC GGA TAT CAT TTG ATC GGT
gly val asp phe gly ser ser ile thr tyr ser cys asn ser gly tyr his leu ile gly
361/121                                391/131
GAA TCT AAA TCG TAT TGT GAA TTA GGA TCT ACT GGA TCT ATG GTA TGG AAT CCC GAG GCA
glu ser lys ser tyr cys glu leu gly ser thr gly ser met val trp asn pro glu ala
421/141                                451/151
CCT ATT TGT GAA TCT GTT AAA TGC CAA TCC CCT CCA TCT ATA TCC AAC GGA AGA CAT AAC
pro ile cys glu ser val lys cys gln ser pro pro ser ile ser asn gly arg his asn
481/161                                511/171
GGA TAC GAG GAT TTT TAT ACC GAT GGG AGC GTT GTA ACT TAT AGT TGC AAT AGT GGA TAT
gly tyr glu asp phe tyr thr asp gly ser val val thr tyr ser cys asn ser gly tyr
541/181                                571/191
TCG TTG ATT GGT AAC TCT GGT GTC CTG TGT TCA GGA GGA GAA TGG TCC GAT CCA CCC ACG
ser leu ile gly asn ser gly val leu cys ser gly gly glu trp ser asp pro pro thr
601/201                                631/211
TGT CAG ATT GTT AAA TGT CCA CAT CCT ACA ATA TCA AAC GGA TAC TTG TCT AGC GGG TTT
cys gln ile val lys cys pro his pro thr ile ser asn gly tyr leu ser ser gly phe
661/221                                691/231
AAA AGA TCA TAC TCA TAC AAC GAC AAT GTA GAC TTT AAG TGC AAG TAC GGA TAT AAA CTA
lys arg ser tyr ser tyr asn asp asn val asp phe lys cys lys tyr gly tyr lys leu
721/241                                751/251
TCT GGT TCC TCA TCA TCT ACT TGC TCT CCA GGA AAT ACA TGG AAG CCG GAA CTT CCA AAA
ser gly ser ser ser ser thr cys ser pro gly asn thr trp lys pro glu leu pro lys
781/261
TGT GTA CGC
cys val arg
```

FIG. 1

Variola major virus    -> 1-phase Translation

DNA sequence  792 b.p.  ATGAAGGTGGAG . . . TGTGTACGCTAA  linear

```
1/1                                       31/11
ATG AAG GTG GAG AGA GTG ACG TTC CTG ACA TTG TTG GGA ATA GGA TGC GTT CTA TCA TGC
Met lys val glu arg val thr phe leu thr leu leu gly ile gly cys val leu ser cys
61/21                                     91/31
TGT ACT ATT CCG TCA CGA CCC ATT AAT ATG AAA TTT AAG AAT AGT GTG GAG ACT GAT GCT
cys thr ile pro ser arg pro ile asn met lys phe lys asn ser val glu thr asp ala
121/41                                    151/51
AAT GCT AAT TAC AAC ATA GGA GAC ACT ATA GAA TAT CTA TGT CTA CCT GGA TAC AGA AAG
asn ala asn tyr asn ile gly asp thr ile glu tyr leu cys leu pro gly tyr arg lys
181/61                                    211/71
CAA AAA ATG GGA CCT ATA TAT GCT AAA TGT ACA GGT ACT GGA TGG ACA CTC TTT AAT CAA
gln lys met gly pro ile tyr ala lys cys thr gly thr gly trp thr leu phe asn gln
241/81                                    271/91
TGT ATT AAA CGG AGA TGC CCG TCG CCT CGA GAT ATC GAT AAT GGC CAT CTT GAT ATT GGC
cys ile lys arg arg cys pro ser pro arg asp ile asp asn gly his leu asp ile gly
301/101                                   331/111
GGA GTA GAC TTT GGC TCT AGT ATA ACG TAC TCT TGT AAT AGC GGA TAT TAT TTG ATT GGT
gly val asp phe gly ser ser ile thr tyr ser cys asn ser gly tyr tyr leu ile gly
361/121                                   391/131
GAA TAT AAA TCG TAT TGT AAA TTA GGA TCT ACT GGA TCT ATG GTA TGG AAT CCC AAG GCA
glu tyr lys ser tyr cys lys leu gly ser thr gly ser met val trp asn pro lys ala
421/141                                   451/151
CCT ATT TGC GAA TCT GTT AAA TGC CAA TTA CCT CCA TCT ATA TCC AAC GGA AGA CAT AAC
pro ile cys glu ser val lys cys gln leu pro pro ser ile ser asn gly arg his asn
481/161                                   511/171
GGA TAT AAT GAT TTT TAT ACC GAT GGA AGC GTT GTA ACT TAT AGT TGC AAT AGT GGA TAT
gly tyr asn asp phe tyr thr asp gly ser val val thr tyr ser cys asn ser gly tyr
541/181                                   571/191
TCG TTG ATT GGT AAC TCT GGT GTC CTG TGT TCA GGA GGA GAA TGG TCT AAT CCA CCC ACG
ser leu ile gly asn ser gly val leu cys ser gly gly glu trp ser asn pro pro thr
601/201                                   631/211
TGT CAG ATT GTT AAA TGT CCA CAT CCT ACA ATA TTA AAC GGA TAC TTG TCT AGC GGG TTT
cys gln ile val lys cys pro his pro thr ile leu asn gly tyr leu ser ser gly phe
661/221                                   691/231
AAA AGA TCA TAT TCG TAT AAT GAC AAT GTA GAC TTT ACG TGC AAG TAC GGA TAT AAA CTA
lys arg ser tyr ser tyr asn asp asn val asp phe thr cys lys tyr gly tyr lys leu
721/241                                   751/251
TCT GGT TCC TCA TCA TCT ACT TGC TCT CCA GGA AAT ACA TGG CAA CCG GAA CTT CCA AAA
ser gly ser ser ser ser thr cys ser pro gly asn thr trp gln pro glu leu pro lys
781/261
TGT GTA CGC TAA
cys val arg OCH
```

FIG. 2

SPICE From VCP copy -> 1-phase Translation

DNA sequence 789 b.p.     ATGAAGGTGGAG ... AAATGTGTACGC     linear

```
1/1                                     31/11
ATG AAG GTG GAG AGC GTG ACG TTC CTG ACA TTG TTG GGA ATA GGA TGC GTT CTA TCA TGC
Met lys val glu ser val thr phe leu thr leu leu gly ile gly cys val leu ser cys
61/21                                   91/31
TGT ACT ATT CCG TCA CGA CCC ATT AAT ATG AAA TTT AAG AAT AGT GTG GAG ACT GAT GCT
cys thr ile pro ser arg pro ile asn met lys phe lys asn ser val glu thr asp ala
121/41                                  151/51
AAT GCT AAT TAC AAC ATA GGA GAC ACT ATA GAA TAT CTA TGT CTA CCT GGA TAC AGA AAG
asn ala asn tyr asn ile gly asp thr ile glu tyr leu cys leu pro gly tyr arg lys
181/61                                  211/71
CAA AAA ATG GGA CCT ATA TAT GCT AAA TGT ACA GGT ACT GGA TGG ACA CTC TTT AAT CAA
gln lys met gly pro ile tyr ala lys cys thr gly thr gly trp thr leu phe asn gln
241/81                                  271/91
TGT ATT AAA CGG AGA TGC CCA TCG CCA CGA GAT ATC GAT AAT GGC CAT CTT GAT ATT GGT
cys ile lys arg arg cys pro ser pro arg asp ile asp asn gly his leu asp ile gly
301/101                                 331/111
GGA GTA GAC TTT GGC TCT AGT ATA ACG TAC TCT TGT AAT AGC GGA TAT TAT TTG ATC GGT
gly val asp phe gly ser ser ile thr tyr ser cys asn ser gly tyr tyr leu ile gly
361/121                                 391/131
GAA TAT AAA TCG TAT TGT AAA TTA GGA TCT ACT GGA TCT ATG GTA TGG AAT CCC AAG GCA
glu tyr lys ser tyr cys lys leu gly ser thr gly ser met val trp asn pro lys ala
421/141                                 451/151
CCT ATT TGT GAA TCT GTT AAA TGC CAA TTG CCT CCA TCT ATA TCC AAC GGA AGA CAT AAC
pro ile cys glu ser val lys cys gln leu pro pro ser ile ser asn gly arg his asn
481/161                                 511/171
GGA TAC AAT GAT TTT TAT ACC GAT GGG AGC GTT GTA ACT TAT AGT TGC AAT AGT GGA TAT
gly tyr asn asp phe tyr thr asp gly ser val val thr tyr ser cys asn ser gly tyr
541/181                                 571/191
TCG TTG ATT GGT AAC TCT GGT GTC CTG TGT TCA GGA GGA GAA TGG TCC AAT CCA CCC ACG
ser leu ile gly asn ser gly val leu cys ser gly gly glu trp ser asn pro pro thr
601/201                                 631/211
TGT CAG ATT GTT AAA TGT CCA CAT CCT ACA ATA TTA AAC GGA TAC TTG TCT AGC GGG TTT
cys gln ile val lys cys pro his pro thr ile leu asn gly tyr leu ser ser gly phe
661/221                                 691/231
AAA AGA TCA TAC TCA TAC AAC GAC AAT GTA GAC TTT ACG TGC AAG TAC GGA TAT AAA CTA
lys arg ser tyr ser tyr asn asp asn val asp phe thr cys lys tyr gly tyr lys leu
721/241                                 751/251
TCT GGT TCC TCA TCA TCT ACT TGC TCT CCA GGA AAT ACA TGG CAG CCG GAA CTT CCA AAA
ser gly ser ser ser ser thr cys ser pro gly asn thr trp gln pro glu leu pro lys
781/261
TGT GTA CGC
cys val arg
```

FIG. 3

```
VCP/SPICE DNA and Protein sequence
VCP amino acid sequence                                              M  K  V  E  S  V  T  F  L  T  L  L  G
VCP sense           TTTTTATTATTTGTACGATGTCCAGGATAACATTTTTACGGATAAATAAATATGAAGGTGGAGAGCGTGACGTTCCTGACATTGTTGGGA
VCP antisense       AAAAATAATAAACATGCTACAGGTCCTATTGTAAAAATGCCTATTTATTTATACTTCCACCTCTCGCACTGCAAGGACTGTAACAACCCT
SPICE amino acid/#                                                   M  K  V  E [R] V  T  F  L  T  L  L  G 13
nucleotide #                  10        20        30        40        50        60        70        80        90

SCR-1>
VCP amino acid sequence  I  G  C  V  L  S | C [C] T  I  P  S  R  P  I  N  M  K  F  K  N  S  V  E  T  D  A  N  A  N
VCP sense           ATAGGATGCGTTCTATCA|TGCTGTACTATTCCGTCACGACCCATTAATATGAAATTTAAGAATAGTGTGGAGACTGATGCTAATGCTAAT
VCP antisense       TATCCTACGCAAGATAGT|ACGACATGATAAGGCAGTGCTGGGTAATTATACTTTAAATTCTTATCACACCTCTGACTACGATTACGATTA
SPICE amino acid/#       I  G  C  V  L  S | C  C  T  I  P  S  R  P  I  N  M  K  F  K  N  S  V  E  T  D  A  N  A  N 43
nucleotide #                  100       110       120       130       140       150       160       170       180

VCP amino acid sequence  Y  N  I  G  D  T  I  E  Y  L [C] L  P  G  Y  R  K  Q  K  M  G  P  I  Y  A  K [C] T  G  T
VCP sense           TACAACATAGGAGACACTATAGAATATCTATGTCTACCTGGATACAGAAAGCAAAAAATGGGACCTATATATGCTAAATGTACAGGTACT
VCP antisense       ATGTTGTATCCTCTGTGATATCTTATAGATACAGATGGACCTATGTCTTTCGTTTTTTACCCTGGATATATACGATTTACATGTCCATG#
SPICE amino acid/#       Y  N  I  G  D  T  I  E  Y  L  C  L  P  G  Y  R  K  Q  K  M  G  P  I  Y  A  K  C  T  G  T 73
nucleotide #                  190       200       210       220       230       240       250       260       270

SCR-2>
VCP amino acid sequence  G  W  T  L  F  N  Q [C] I  K  R  R [C] P  S  P  R  D  I  D  N  G  Q  L  D  I  G  G  V  D
VCP sense           GGATGGACACTCTTTAATCAATGTATTAAACGGAGATGCCCATCGCCTCGAGATATCGATAATGGCCAACTTGATATTGGTGGAGTAGAC
VCP antisense       CCTACCTGTGAGAAATTAGTTACATAATTTGCCTCTACGGGTAGCGGAGCTCTATAGCTATTACCGGTTGAACTATAACCACCTCATCTG SPICE amino acid/#       G  W  T  L  F  N  Q  C  I  K  R  R  C  P  S  P  R  D     D  N  G [H] L  D  I  G  G  V  D 103
potential codon changes                                                                  CAC
potential codon changes                                                                  CAT
nucleotide #                  280       290       300       310       320       330       340       350       360
```

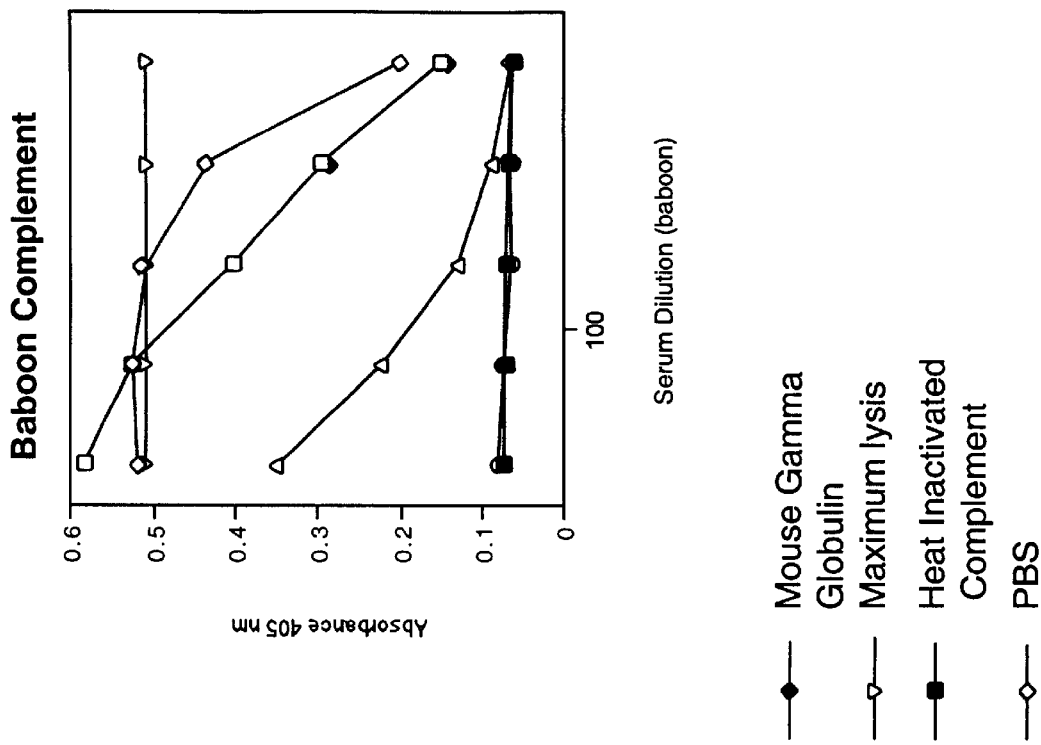
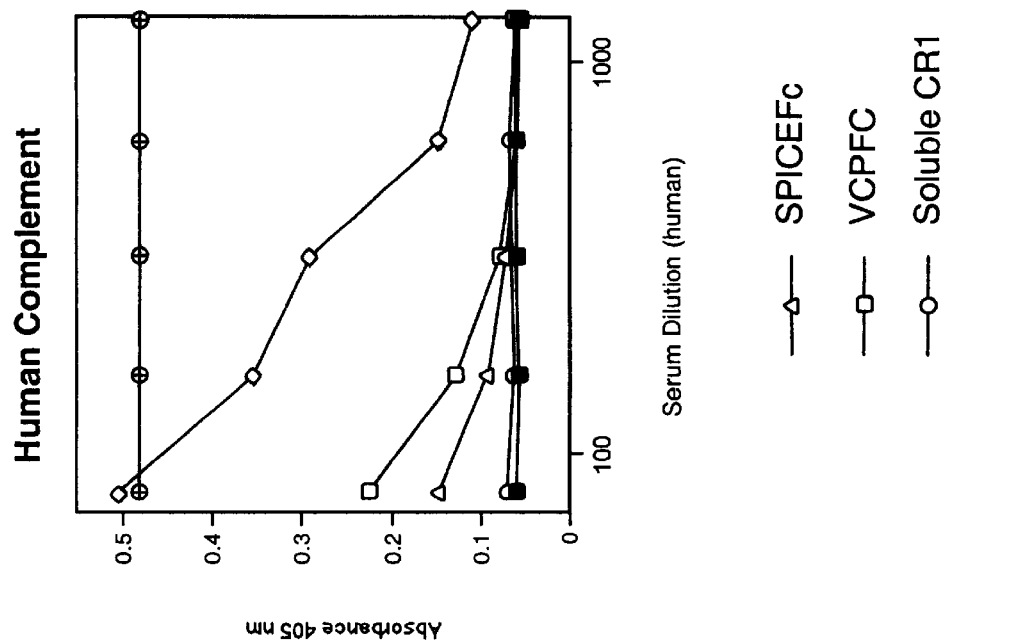

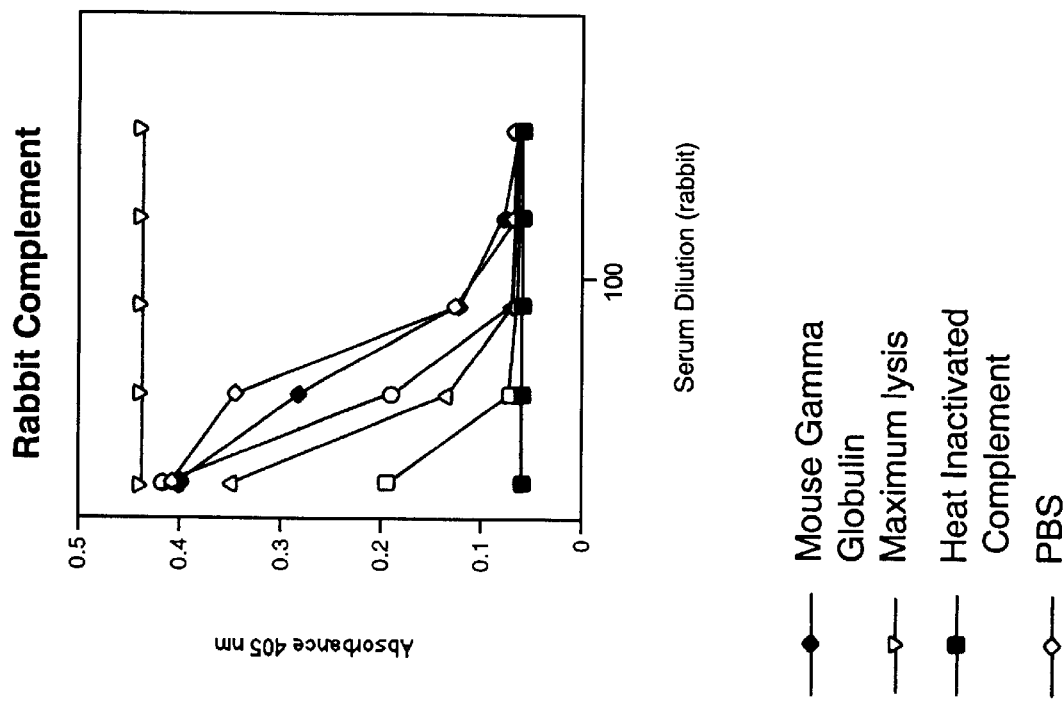
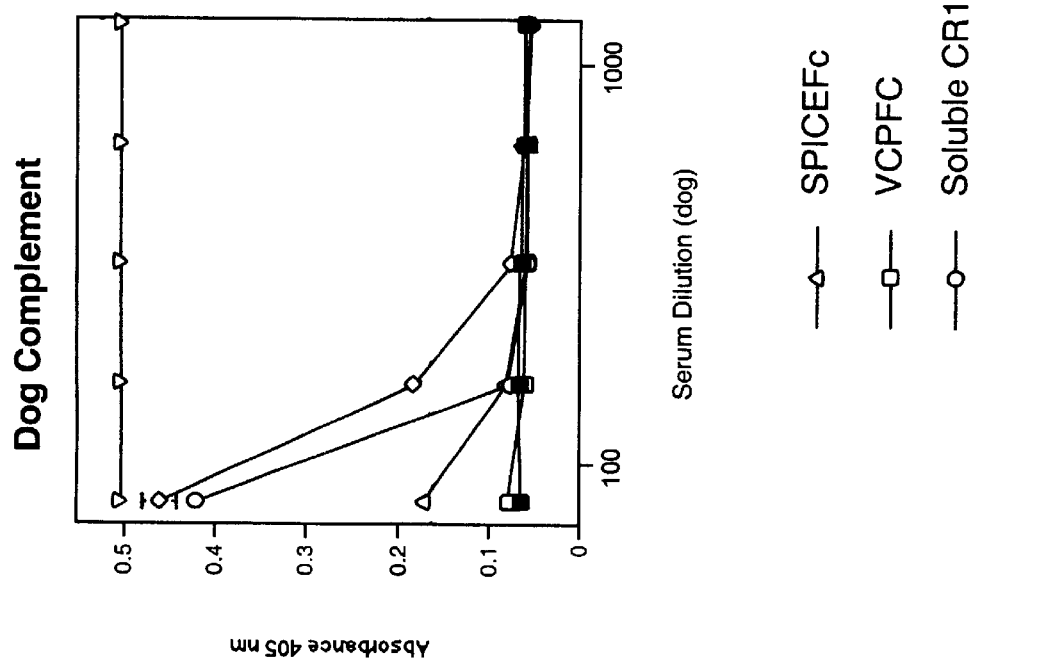

SMALLPOX INHIBITOR OF COMPLEMENT ENZYMES (SPICE) PROTEIN AND METHODS OF INHIBITING COMPLEMENT ACTIVATION

This application is a continuation of PCT/US99/04635, filed Mar. 2, 1999, which claims the benefit of U.S. provisional application Ser. No. 60/076,821, filed Mar. 3, 1998.

FIELD OF THE INVENTION

The field of the invention is inhibition of complement activation.

BACKGROUND OF THE INVENTION

The complement system plays a fundamental role in both the innate and acquired immune responses. As such, it also participates in the majority of diseases characterized by acute and/or chronic inflammation. For example, a critical role of the complement system has been demonstrated in rheumatoid arthritis, post-myocardial infarction reperfusion injury, post-bowel ischemia reperfusion injury, and systemic lupus erythematosus. These specific disorders are simply representative of most inflammatory states in which similar or identical molecular pathways result in complement activation and concomitant tissue injury.

Hyperacute rejection of xenografts has also been shown to result from activation of the human complement system. The utilization of organs obtained from nonhuman donors is an appealing solution to the increasing shortage of organs available for clinical transplantation. Although xenotransplantation using organs obtained from primate donors has been performed with limited clinical success, the use of distantly related species, such as pigs or sheep, avoids ethical dilemmas, potential virus transmission, and limited availability associated with the use of primates as xenograft donors. However, the use of organs from distantly related species for xenotransplantation is impractical due to hyperacute rejection (hyperacute rejection), a process that leads to irreversible xenograft damage and organ loss within minutes to hours. In xenotransplantation of vascularized tissues, hyperacute rejection is thought to be mediated by the binding of naturally occurring recipient antibodies to the endothelium of the xenograft.

The fundamental molecular basis for hyperacute rejection is thought to be activation of the classical pathway of the human complement system by human antibodies directed to immunologically foreign epitopes present on donor endothelial cells. In pig to primate xenotransplantation, it has been demonstrated that primate antibodies are primarily directed to a post-translational modification of pig membrane proteins, which modification does not occur in human cells. Specifically, foreign epitopes are generated by oligosaccharide moieties containing galactose ($\alpha$1–3) galactose, the result of a swine enzyme that is not present in human cells. In some combinations of discordant species, activation of the alternative pathway of complement also participates in hyperacute rejection. Activation of either the classical pathway or the alternative pathway of complement leads to endothelial cell activation, thrombosis, intravascular coagulation, edema, and eventual loss of function and rejection of the transplanted organ.

The fundamental role of the complement system during hyperacute rejection has led to investigations of the potential to prevent hyperacute rejection through the use of recombinant inhibitors of the human complement system. Initial studies focused upon the use of naturally occurring endogenous human complement regulatory proteins.

Human cells and tissues are protected from inadvertent complement-mediated injury by a diverse and apparently redundant family of regulatory molecules, most of which belong to the regulators of complement activation (RCA) family. One primary function of these molecules is to inhibit formation and accumulation of C3b, which is a product of C3 cleavage by either the classical (C4b2a) or the alternative (C3bBb) pathway convertase. In general, RCA proteins can be viewed as either function-specific or pathway-specific. For example, proteins such as decay accelerating factor (DAF; CD55) and membrane cofactor protein (MCP; CD46) are capable of regulating both the alternative and classical pathways, yet each has a limited functional role by performing either decay or cofactor function, respectively. DAF acts to dissociate the components within each of the bimolecular enzymes, whereas MCP acts as a cofactor for the serine protease factor I that cleaves C3b to form C3bi which is incapable of further participation in the complement cascade. In contrast, Factor H and C4b binding protein function specifically within the alternative pathway and classical pathway, respectively, yet each protein provides both MCP- and DAF-like control in this regard. Complement receptor type 1 (CR1) is the most versatile human complement inhibitor; it serves to regulate both the alternative pathway and classical pathway having decay and cofactor activities, and also provides a clearance function. for C3- or C4-bearing complexes which, following inactivation, it retains and transports to the reticuloendothelial system for degradation.

The functional domains of CRI, DAF, MCP, and all other RCA family members consist of repeating modules termed short consensus repeats (SCRs). Each SCR contains approximately 60 amino acids that form hypervariable domains as well as highly conserved regions. Electron microscopic studies of CRI and other family members have demonstrated that the multiple SCRs within an individual protein are tandemly arranged end to end, with each SCR representing a discrete structural unit. Each RCA family member is composed of multiple SCRs ranging from 4 SCRS in the case of DAF and MCP, to 30 SCRs in the case of the most common allotype of CR1. Amino acid homology between any two SCRs within the family ranges from 10% to 99%. These structural features of SCRs translate into the functionally conserved capacity among family members to bind C3b as well as the functionally diverse consequences of this interaction as described above.

It has been demonstrated that transgenic expression of human endogenous complement regulatory proteins (e.g. DAF, CD59) on xenografts may diminish or prevent hyperacute rejection. The human proteins that were initially chosen for these studies were presumably selected because they were among the first complement regulatory proteins to be discovered, rather than for any particular function or combinations of functions. As described above, RCA proteins are classified in three ways. A given RCA protein is described in terms of its ligands, its capacity to provide cofactor and/or decay accelerating activity, and its capacity to inhibit the alternative pathway, the classical pathway or both (Table 1). All of the RCA proteins described in Table 1 demonstrate some degree of functional versatility by inhibiting complement activation at more than one point in the cascade. Similarly, CR1 is considered the most versatile inhibitor.

TABLE 1

Functional Categorization of Human Complement Regulatory Proteins

| Inhibitor | Ligand(s) | Function | Pathway |
|---|---|---|---|
| DAF | C3b? | D | AP, CP |
| MCP | C3b | C | AP, CP |
| CR1 | C3b, iC3b, C4b | D, C, IC | AP, CP |
| H | C3b | D, C | AP |
| C4bp | C4b | D, C | CP |

D = Decay Acceleration;
C = Factor I Cofactor;
AP = Alternative Pathway;
CP = Classical Pathway;
IC = Immune Complex Clearance Recombinant versions of regulators of complement activation have been reported. Hebel et al. (WO 91/16437, Oct. 31, 1991) describe soluble peptide analogs containing binding sites for complement. Kotwal et al. (1990, Science 250:827–830) describe a gene encoding the anti-complement protein, vaccinia virus complement control protein (VCP) (U.S. Pat. No. 5,187,268, Feb. 16, 1993), a 35 kD protein that is secreted by cells infected with vaccinia. Structurally, VCP consists entirely of four SCRs which bear 35% and 31% amino acid identity to MCP and DAF, respectively. Several studies over the past few years have demonstrated that VCP is capable of inhibiting the classical and alternative pathways through both decay and cofactor activities.

Historically, vaccinia virus was used as a vaccine to protect against infection by variola virus, the etiologic agent of smallpox. The amino acid sequence homology between most of the proteins in the two viruses is approximately 95%.

The virus that causes smallpox has been completely eradicated in that the last confirmed case of naturally occurring smallpox was reported in Somalia in October 1977. However, samples of the virus are maintained at two locations: The Centers for Disease Control in Atlanta, Ga., U.S.A. and The Russian State Research Center for Virology and Biotechnology at NPO Vector Koltsovo, Novosibirsk Region, Russia. These samples generally are not available to scientists for study. Indeed, the destruction of these samples has been the subject of serious medical and scientific debate. Consequently, little is known about the expression or function of the polypeptides encoded by the variola genome.

The variola genome is discussed in Massung et al. (1993, Nature 366:748–751). The nucleotide sequence of the genome was released into Medline (Accession No. L22579), apparently in 1995. The sequence includes an open reading frame that encodes a polypeptide with an amino acid sequence similar to the vaccinia complement inhibiting protein, VCP. The nucleotide sequences differ in twenty-six base pairs, all of which are located in the last three SCRs of VCP. However, because variola is not available for study, researchers do not know whether the variola protein has any biological activity or whether, indeed, it is produced at all. Although one might conclude that all SCR containing proteins should have some complement inhibitory activity, this is in fact not the case. For example, in addition to VCP, vaccinia virus encodes another SCR containing protein named B5R, which to date, has not been shown to exhibit any complement inhibitory activity (Herrera et al., 1998, J. Virol. 72:294–302). It was therefore necessary to produce and test the variola protein of the present invention (encoded by four SCRs) for complement inhibitory activity before concluding that it had any regulatory effect on complement.

While the complement system is essential for normal immune function in a mammal, activation of complement in certain situations may play a detrimental role in the mammal. There is a need in the art for compositions and methods which modulate complement activation, in particular, for compositions and methods which inhibit complement activation, in order that complement activation may be controlled in situations which are detrimental to a mammal. The present invention satisfies this need.

SUMMARY OF THE INVENTION

Using site-specific mutagenesis directed to a gene encoding VCP, a polynucleotide has been generated in the present invention that encodes a polypeptide which is believed to be the polypeptide encoded by an open reading frame in a published variola genome. The full-length polypeptide includes a signal sequence followed by four short consensus repeats. The short consensus repeats include four cysteine residues characteristic of the short consensus repeats of many complement binding proteins, such as CR1, CR2, C4bp, DAF, MCP and VCP. When produced as a fusion protein in which the four SCRs of the protein are attached to a chain of the Fc portion of an immunoglobulin, the protein inhibits human complement activation. The protein has greater complement-inhibiting activity than VCP.

The protein of the invention has been named "SPICE," for Smallpox Inhibitor of Complement Enzymes. SPICE and proteins derived from it, are useful for the inhibition of complement activation in vitro, ex vivo and in vivo. As such, the complement inhibitors of the present invention are useful for the treatment of complement-mediated conditions. Such conditions include, but are not limited to, hyperacute rejection, as well as inflammatory diseases in which complement recruits inflammatory mediators, and reperfusion injuries.

In in vitro use, the complement inhibitors of the invention are useful for the prevention of complement-mediated damage to blood cells and for the study of complement activity.

In one aspect, the invention provides an isolated and substantially pure preparation of smallpox inhibitor of complement enzymes (SPICE) protein (SEQ ID NO:4). In another aspect, the invention provides a substantially pure preparation of a fragment of smallpox inhibitor of complement enzymes (SPICE) protein (SEQ ID NO:4), the fragment comprising at least a complement-inhibiting portion of SPICE, the portion including four short consensus repeats (SCRs) of SPICE, wherein the protein inhibits complement activation.

In another aspect, the invention provides a SPICE-related fusion protein comprising at least one polypeptide moiety attached to at least a complement-inhibiting portion of smallpox inhibitor of complement enzymes (SPICE) protein (SEQ ID NO:4), the portion including four short consensus repeats (SCRs) of SPICE, wherein the protein inhibits complement activation. In one embodiment, the polypeptide moiety increases the half-life of the protein in the human circulatory system to at least about 2 days. In another embodiment, the polypeptide moiety comprises at least a portion of an Fc molecule sufficient to bind protein A and protein G. In yet another embodiment, the polypeptide moiety comprises a signal sequence that causes secretion of the protein from a cell upon expression of the protein in the cell. In another embodiment, the polypeptide moiety comprises a transmembrane region that attaches the protein as expressed to a cell surface. In yet another embodiment, the portion of SPICE is fused to at least a transmembrane region of a regulator of complement activation selected from CR1, CR2, DAF and MCP. In yet another embodiment, the polypeptide moiety comprises at least one complement-binding SCR of a regulator of complement activation selected from the group consisting of Factor H, C4bp, CR1, CR2, DAF, MCP and VCP. In another embodiment, the portion of SPICE replaces (1) SCR1 and SCR2 of CR2 in a full-length membrane-bound or soluble CR2 protein, (2) SCRs 1–4, SCRs 8–11 or SCRs 15–18 of CR1 in a full-length membrane-bound or soluble CR1 protein or (3) at least one SCR of C4bp in a full-length C4bp polypeptide. In another embodiment, the fusion protein comprises a SPICE multimer, wherein the polypeptide moiety comprises at least one complement-inhibiting portion of SPICE. In another embodiment, the polypeptide moiety comprises a ligand that specifically binds a target receptor. In another embodiment, the polypeptide moiety comprises at least a variable region of an immunoglobulin molecule or at least a portion of an Fc molecule sufficient to bind a cell surface Fc receptor. In another embodiment, the polypeptide moiety comprises at least one constant region domain selected from $CH_1$, $CH_2$, and $CH_3$, of an immunoglobulin molecule, and the protein further comprises a second polypeptide attached to the fusion protein that comprises at least a variable region of an immunoglobulin molecule, the variable region specifically binding to a ligand.

In another aspect, the invention provides a variola-regulator of complement activation (RCA) chimeric protein. The chimeric protein of the invention comprises at least one SCR from SPICE (i.e., SCR2, SCR3 or SCR4) and at least one SCR from an RCA (e.g., CR1, CR2, C4bp, DAF, MCP, Factor H and VCP). The SCRs are selected so that the chimeric protein inhibits complement activation. In one embodiment, the chimeric protein has four SCRs wherein the SCRs comprise at least one SCR from VCP and at least one SCR selected from SCR2, SCR3 or SCR4 of SPICE.

In another aspect, the invention provides a recombinant polynucleotide comprising a nucleotide sequence encoding a polypeptide that inhibits human complement activation. The polypeptide comprises at least a complement-inhibiting portion of SPICE protein (SEQ ID NO:4), the portion includes four short consensus repeats (SCRs) of SPICE. The nucleotide sequence comprises a mutated vaccinia complement control protein (VCP) sequence (SEQ ID NO: 1) encoding the portion of SPICE and substituted with codons encoding amino acid substitutions: Q96H, H117Y, S122Y, E127K, E139K, S150L, E163N, D197N, S212L, K233T, and K255Q (referring to SEQ ID NO:2). In one embodiment, the mutated VCP sequence encoding the portion of SPICE is a sequence selected from SEQ ED NO:5. In another embodiment, the recombinant polynucleotide further comprises an expression control sequence operatively linked to the nucleotide sequence. In another embodiment, the expression control sequence is operative in a mammalian cell. In another embodiment the recombinant polynucleotide is comprised within an adenoviral vector, an adeno-associated viral vector, or a retroviral vector.

In another aspect, the invention provides a recombinant cell comprising the recombinant polynucleotide of the invention. In one embodiment, the recombinant cell is a mammalian cell.

In another aspect, the invention provides a pharmaceutical composition comprising a pharmaceutically acceptable carrier and a protein inhibitor of complement activation in an amount effective to inhibit human complement activation. The protein is: (a) smallpox inhibitor of complement enzymes (SPICE) protein (SEQ ID NO:4), (b) a fragment of SPICE, the fragment comprising at least a complement-inhibiting portion of SPICE, the portion including four short consensus repeats (SCRs) of SPICE, wherein the protein inhibits complement activation or (c) a SPICE-related fusion protein comprising at least one polypeptide moiety attached to at least a complement-inhibiting portion of SPICE, the portion including four SCRs of SPICE.

In another aspect, the invention provides a transgenic, non-human in mammal whose germ cells at least comprise a recombinant polynucleotide comprising an expression control sequence operative in the mammal and operatively linked to a nucleotide sequence encoding a polypeptide that inhibits human complement activation, wherein the polypeptide comprises at least a complement-inhibiting portion of smallpox inhibitor of complement enzymes (SPICE) protein (SEQ ID NO:4), the portion including four short consensus repeats (SCRs) of SPICE. In one embodiment, the non-human mammal is a non-human primate, a pig or a sheep.

In another aspect, the invention provides a graft comprising cells from a non-human mammal, the cells comprising a recombinant polynucleotide comprising an expression control sequence operative in the mammal and operatively linked to a nucleotide sequence encoding a polypeptide that inhibits human complement activation, wherein the polypeptide comprises at least a complement-inhibiting portion of smallpox inhibitor of complement enzymes (SPICE) protein (SEQ ID NO:4), the portion including four short consensus repeats (SCRs) of SPICE. In one embodiment the cells are cells from heart, lung, kidney, liver, intestine, pancreas or neural tissue.

In another aspect, the invention provides a method of making a polynucleotide comprising a nucleotide sequence encoding a polypeptide comprising at least a complement-inhibiting portion of smallpox inhibitor of complement enzyme SPICE) (SEQ ID NO:4) comprising the step of introducing into vaccinia complement control protein VCP gene sequence (SEQ ID NO:1) mutations that effect the following codon substitutions: Q96H, H117Y, S122Y, E127K, E139K, S150L, E163N, D197N, S212L, K233T, and K255Q (referring to SEQ ID NO:2). In one embodiment, the substitutions are: A288T, C349T, C365A, G379A, G415A, C449T, C450T, G487A, G489T, G589A, C635T, A698C, A763C (referring to SEQ ID NO:1).

In another aspect, the invention provides a method of inhibiting complement activation. The method comprises exposing complement to a protein inhibitor of complement activation of the invention in an amount effective to inhibit complement activation. In one embodiment, the method is for the prophylactic or therapeutic treatment of a complement-mediated condition in a human subject comprising the step of administering a pharmacologically effective amount of the protein inhibitor of complement to the subject. In another embodiment, the complement-mediated condition is hyperacute rejection, an inflammatory disorder or a post-ischemic reperfusion condition. In another embodiment, the step of administering comprises administering a vector comprising a recombinant polynucleotide encoding the protein inhibitor of complement, and the vector transfects cells of the subject and the cells express the protein inhibitor of complement.

In another aspect, the invention provides a method of inhibiting complement-mediated hyperacute rejection of a graft for transplantation. The method comprises the step of exposing the graft before implantation to a protein inhibitor of complement activation of the invention in an amount effective to inhibit complement activation. In one embodiment, the step of exposing comprises perfusing an endothelial surface of the graft with a solution comprising the complement inhibitor and a pharmaceutically acceptable carrier.

In another aspect, the invention provides a method of inhibiting hyperacute rejection of a xenograft in a human. The method comprises the step of transplanting into the human a graft comprising cells that express a protein inhibitor of complement of the invention. In one embodiment, the graft comprises organ tissue that expresses the protein as a fusion protein on the surface of endothelial cells.

In another aspect, the invention provides a method of inhibiting complement activation in blood in an extracorporeal blood loop. The method comprises the step of coating the surface of the blood loop that is exposed to blood with a protein inhibitor of complement of the invention.

In another aspect, the invention provides a blood product comprising at least a serum fraction of human blood and an amount of a protein inhibitor of complement activation of the invention.

In yet another aspect, the invention provides a method of inhibiting complement activation in a human blood product, the method comprising the step of administering to the product a protein inhibitor of complement activation of the invention.

BRIEF DESCRIPTION OF THE DRAWINGS

FIG. 1 presents the nucleotide sequence (SEQ ID NO: 1) and deduced amino acid sequence (SEQ ID NO:2) of vaccinia complement control protein (VCP) having a silent T to A transversion at nucleotide position number 267.

FIG. 2 presents the genomic nucleotide sequence (SEQ ID NO:3) and deduced amino acid sequence (SEQ ID NO:4) of smallpox inhibitor of complement enzymes (SPICE) protein.

FIG. 3 presents the vaccinia complement control protein nucleotide sequence mutated to encode SPICE (SEQ ID NO:5), and a deduced amino acid sequence of SPICE (SEQ ID NO:6) in which position 5 is occupied by Ser (from VCP) rather than Arg (from the translated sequence of Massung et al. supra). This leader sequence was not incorporated into the constructs used herein.

FIGS. 4A and 4B represent a comparison between the putative amino acid sequences of VCP (SEQ ID NO:2) (top line) and SPICE (SEQ ID NO:4) (bottom line). Amino acids of SPICE that are different than VCP are indicated in the SPICE line with boxes. Cysteine residues involved in disulfide bonds in the short consensus repeats are indicated with boxes in the VCP sequence. The nucleotide sequence of the vaccinia complement control protein gene (SEQ ID NO:1) is between the amino acid sequences.

Below each putative amino acid of SPICE that is different than an amino acid are nucleotide triplets that could change the amino acid. The codons actually used in the mutated VCP gene are indicated by bold letters. The lightly colored boxes around amino acids in the VCP sequence indicate frequently conserved amino acids within SCRS. The location of the SCRs is also indicated. The numbering refers to the original publication of VCP (Kotwal and Moss, 1988, Nature (Lond.). 335:176–178) and not to the numbering in FIG. 1, 2 or 3.

Figure 5A:
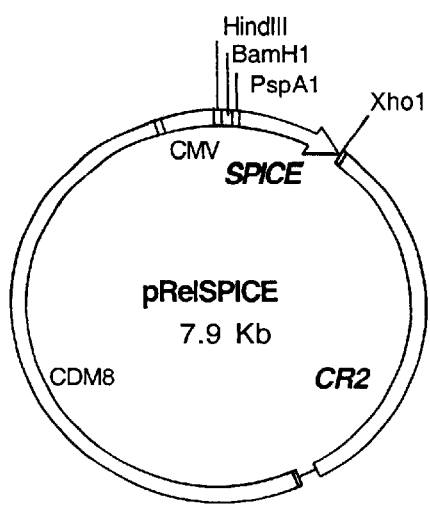
Figure 5B:
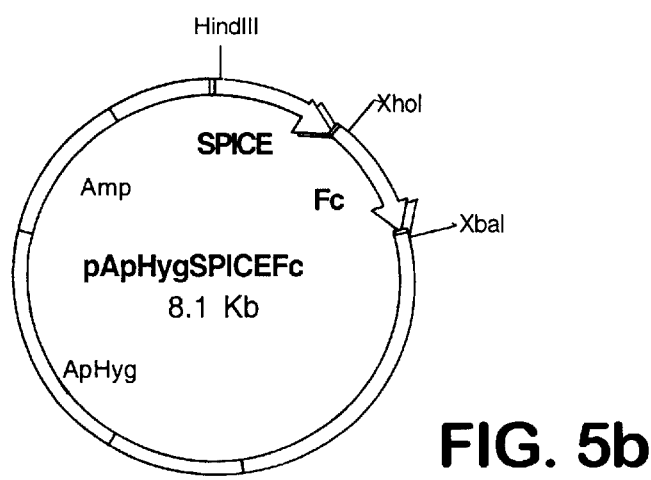
Figure 5C:
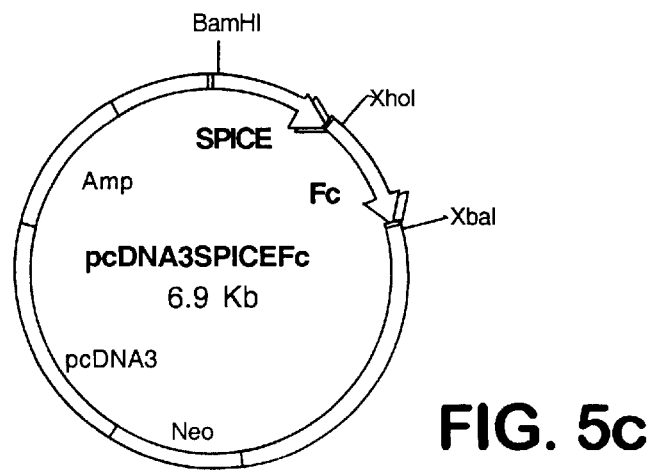

FIGS. 5A–5C are a presentation of a schematic diagram of the SPICE-containing plasmids: a) pRe1SPICE.CR2; b) pApHygSPICEFc; and c) pcDNA3SPICEFc.

Figure 6A:
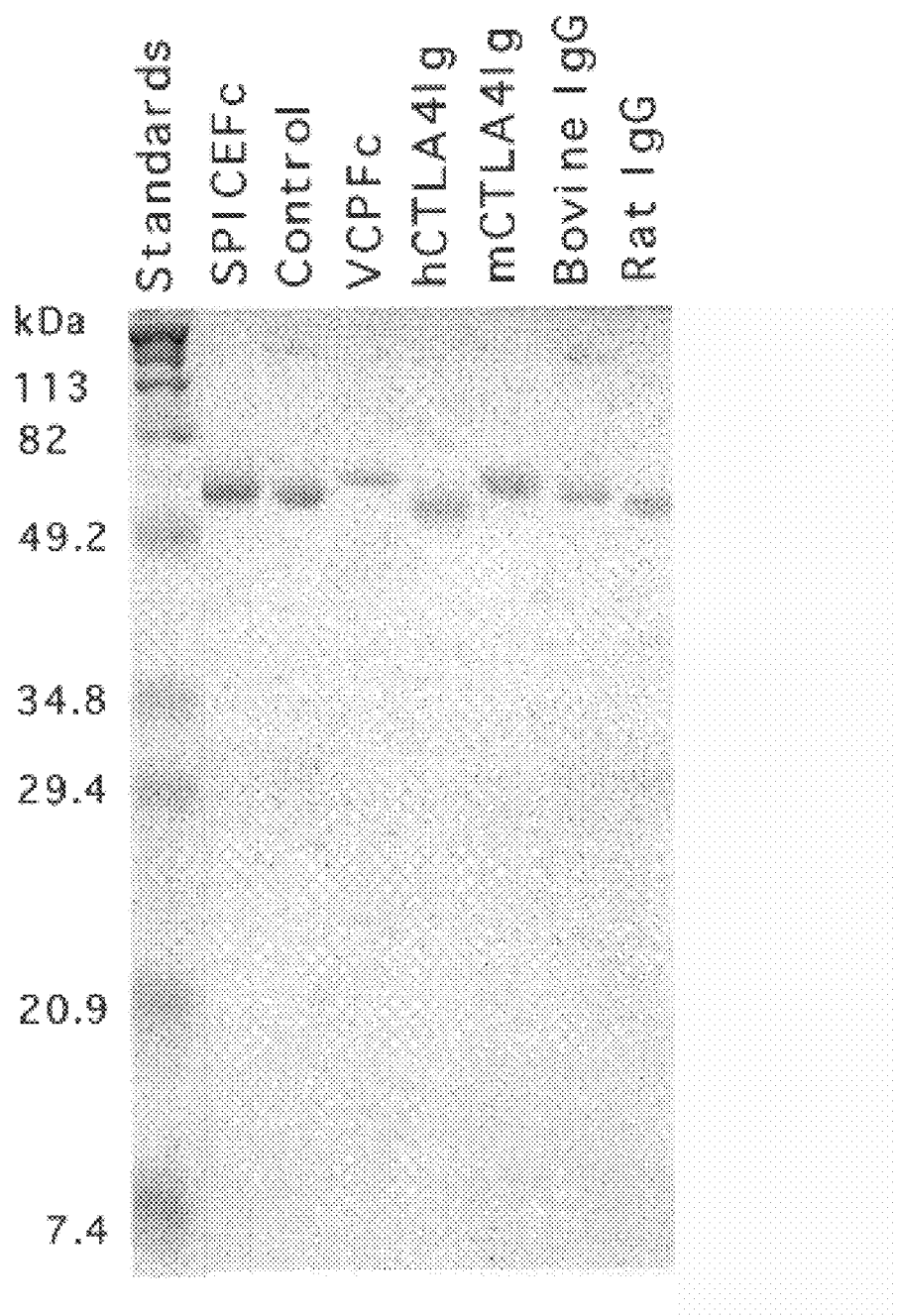
Figure 6B:
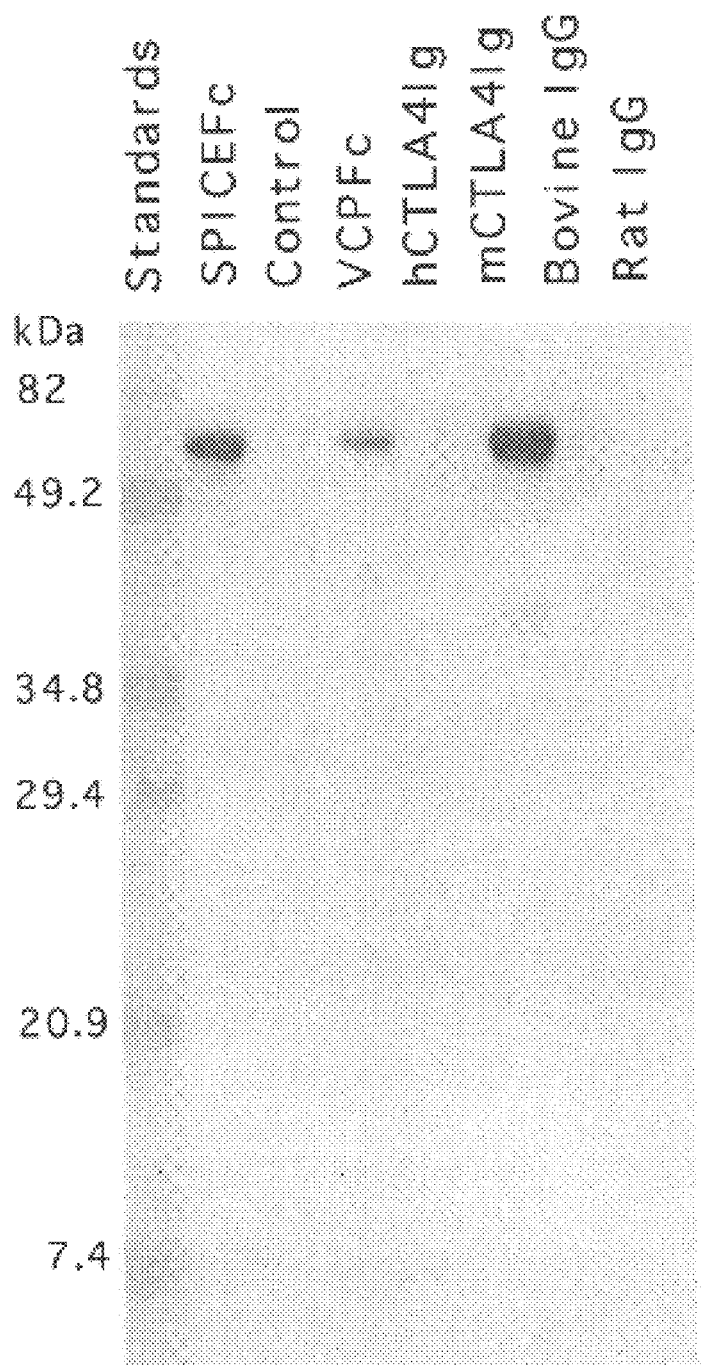
Figure 6C:
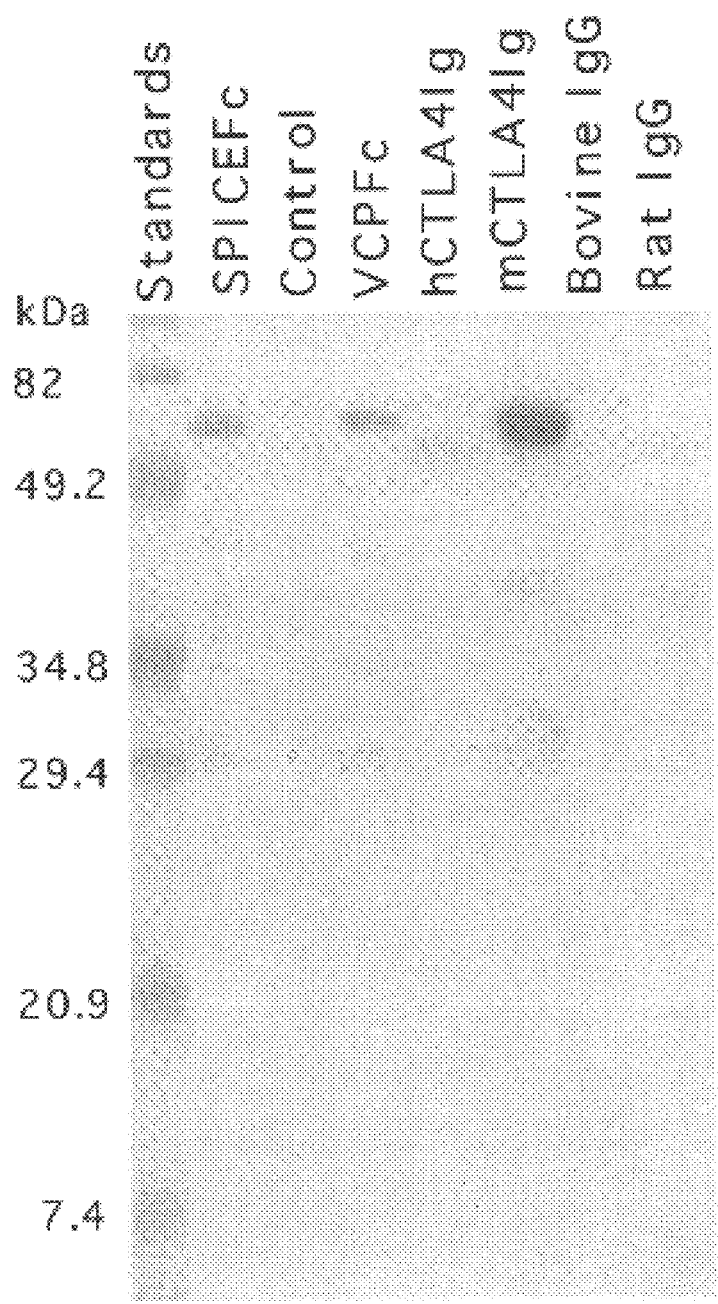

FIGS. 6A–6C are images of Coomassie blue stained polyacrylamide gel (PAGE) and Western blots of SPICEFc. FIG. 6A: PAGE of SPICEFc stained with Coomassie Blue. FIG. 6B: Western blot identification of SPICEFc using anti-mouse Fc antibody. FIG. 6C: Western blot identification of SPICEFc using polyclonal anti-VPCFc antibody.

Figure 7A:
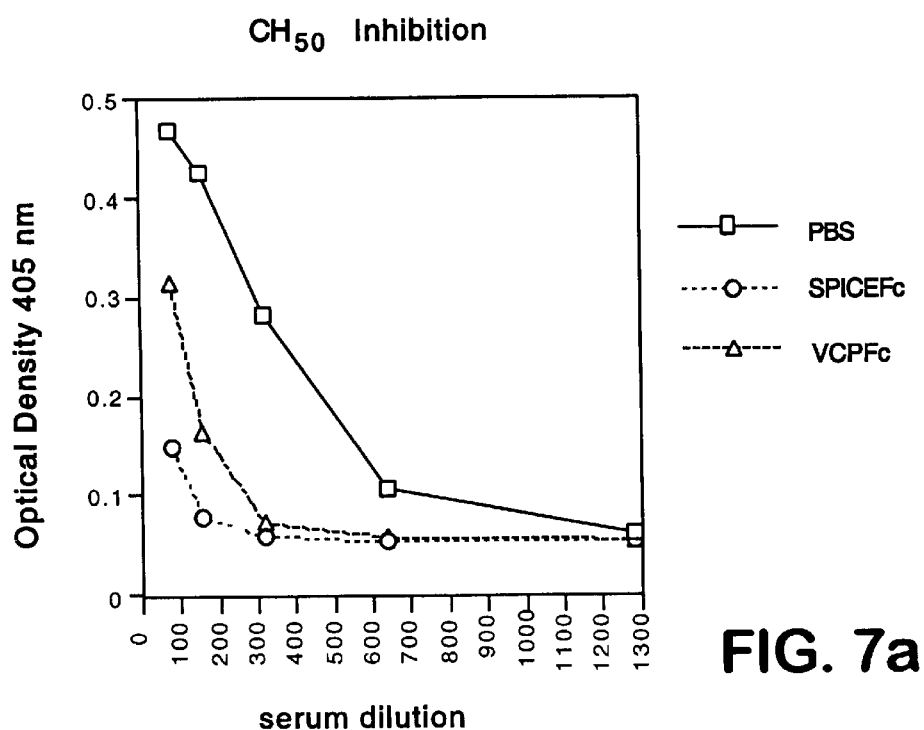
Figure 7B:
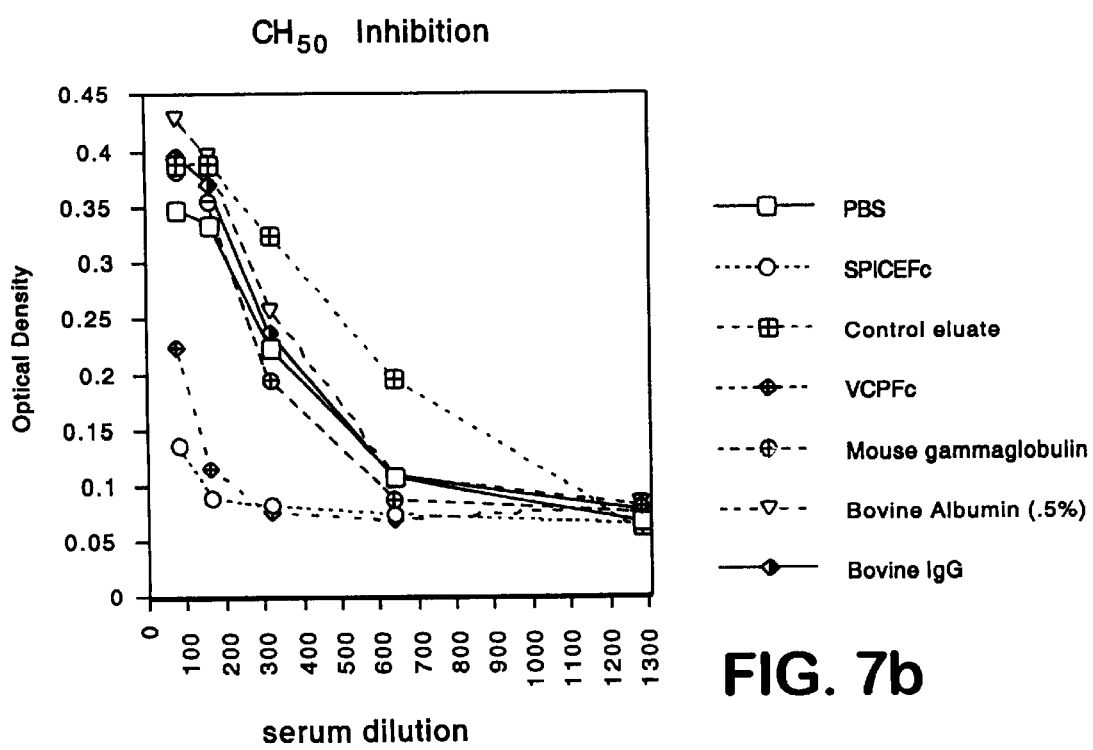

FIGS. 7A–7C are a series of line drawings depicting $CH_{50}$ of sheep erythrocytes which are inhibited using SPICEFC. The optical densities of wells of 96 well plates containing different human serum concentrations, with or without additional protein, were read at 405 nm and plotted in FIGS. 7A–C. SPICEFc is four-fold more effective in inhibiting human complement than is VCPFc.

FIGS. 8A–D are a series of line drawings depicting the fact that SPICEFc and VCPFc exhibit species preference in complement inhibition. Using complement obtained from different species, i.e., human, baboon, dog and rabbit, the $CH_{50}$ of sheep erythrocytes was differentially inhibited by SPICEFc and VCPFc. When compared with each other, SPICEFc was capable of inhibiting primate (human and baboon) complement activation better than the inhibition of primate complement activation by VCPFc. Conversely, VCPFc was capable of inhibiting non-primate (dog or rabbit) complement activation better than the inhibition of non-primate complement activation by SPICEFc. The optical densities of wells of 96 well plates containing different serum concentrations, with or without the complement inhibitor or control protein, were read and plotted in FIGS. 8A–D.

DETAILED DESCRIPTION OF THE INVENTION

Definitions

Unless defined otherwise, all technical and scientific terms used herein have the meaning commonly understood by a person skilled in the art to which the invention belongs. The following references provide one of skill with a general definition of many of the terms used in this invention: Singleton et al., Dictionary of Microbiology and Molecular Biology (2d ed, 1994); The Cambridge Dictionary of Science and Technology (Walker ed., 1988); and Hale & Marham, The Harper Collins Dictionary of Biology (1991). Although any methods and materials similar or equivalent to those described herein can be used in the practice or testing of the present invention, preferred methods and materials are described. As used herein, the following terms have the meanings ascribed to them unless specified otherwise.

The articles "a" and "an" are used herein to refer to one or to more than one (i.e. to at least one) of the grammatical object of the article. By way of example, "an element" means one element or more than one element.

"Plurality" means at least two.

"Polynucleotide" refers to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-0-methyl ribonucleotides, peptide-nucleic acids (PNAs), and the like. Such polynucleotides can be synthesized, for example, using an automated DNA synthesizer.

The polynucleotides of the invention are isolated nucleic acids. An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g, as a cDNA or a genomic or cDNA fragment produced by PCR or restriction enzyme digestion) independent of other sequences. It also includes a recombinant DNA which is part of a hybrid gene encoding additional polypeptide sequence.

The term "nucleic acid" typically refers to large polynucleotides.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an MRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man in the laboratory is naturally-occurring.

Conventional notation is used herein to portray polypeptide sequences: the left-hand end of a polypeptide sequence is the amino-terminus; the right-hand end of a polypeptide sequence is the carboxyl-terminus.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Expression control sequence" refers to a nucleotide sequence in a polynucleotide that regulates the expression (transcription and/or translation) of a nucleotide sequence operatively linked thereto. An expression control sequence may be a promoter sequence or an enhancer sequence, or both. Collectively, such sequences are "promoter/regulatory sequences." As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

"Operatively linked" refers to a functional relationship between two parts in which the activity of one part (e.g., the ability to regulate transcription) results in an action on the other part (e.g. transcription of the sequence). Expression control sequences can include, for example and without limitation, sequences of promoters (e.g., inducible or constitutive), enhancers, transcription terminators, a start codon (i.e., ATG), splicing signals for introns, and stop codons.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

"Recombinant polynucleotide" refers to a polynucleotide having sequences that are not naturally joined together. An amplified or assembled recombinant polynucleotide may be included in a suitable vector, and the vector can be used to transform a suitable host cell.

A host cell that comprises the recombinant polynucleotide is referred to as a "recombinant host cell."

The gene is then expressed in the recombinant host cell to produce, e.g., a "recombinant polypeptide."

A recombinant polynucleotide may serve a non-coding function (e.g., promoter, origin of replication, ribosome-binding site, etc.) as well.

A "ligand" is a compound that specifically binds to a target receptor.

A "receptor" is a compound that specifically binds to a ligand.

"Antibody" refers to a polypeptide substantially encoded by an immunoglobulin gene or immunoglobulin genes, or fragments thereof, which specifically binds and recognizes an epitope (e.g., an antigen). The recognized immunoglobulin genes include the kappa and lambda light chain genes and the alpha, gamma, delta, epsilon and mu heavy chain genes, as well as the myriad immunoglobulin variable region gene segments. Antibodies exist, e.g., as intact immunoglobulin or as a number of well characterized fragments produced by digestion with various peptidases. This includes, e.g., Fab' and F(ab)'fragments. The term "antibody," as used herein, also includes antibody fragments either produced by the modification of whole antibodies or those synthesized de novo using recombinant DNA methodologies. The Fc portion of an antibody refers to that portion of an immunoglobulin heavy chain that comprises one or more heavy chain constant region domains, $CH_1$, $CH_2$, and $CH_3$, but does not include the heavy chain variable region. Thus, the term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1988, Antibodies: A Laboratory Manual, Cold Spring Harbor, N.Y.; Houston et al., 1988, Proc. Natl. Acad. Sci. USA 85:5879–5883; Bird et al., 1988, Science 242:423–426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

A ligand or a receptor (e.g., an antibody) "specifically binds to" or "is specifically immunoreactive with" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to an compound polynucleotide comprising a complementary sequence; an antibody specifically binds under immunoassay conditions to an antigen bearing an epitope against which the antibody was raised. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988, Antibodies, A Laboratory Manual, Cold Spring Harbor Publications, N.Y.) for a description of immunoassay formats and conditions that can be used to determine specific immunoreactivity.

A first sequence is an "antisense" sequence with respect to a second sequence if a polynucleotide whose sequence is the first sequence specifically hybridizes with a polynucleotide whose sequence is the second sequence.

"Substantially pure" means an object species is the predominant species present (i.e., on a molar basis, more abundant than any other individual macromolecular species in the composition) and a substantially purified fraction is a composition wherein the object species comprises at least about 50% (on a molar basis) of all macromolecular species present. Generally, a substantially pure composition means that about 80% to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., bovine serum albumin (BSA)), and elemental ion species are not considered macromolecular species for purposes of this definition.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences.

"Amplification" refers to any means by which a polynucleotide sequence is copied and thus expanded into a larger number of polynucleotide molecules, e.g., by reverse transcription, polymerase chain reaction, and ligase chain reaction.

"Pharmaceutical composition" refers to a composition suitable for pharmaceutical use in a mammal. A pharmaceutical composition comprises a pharmacologically effective amount of an active agent and a pharmaceutically acceptable carrier.

"Pharmacologically effective amount" refers to that amount of an agent effective to produce the intended pharmacological result.

"Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 19th Ed. (Mack Publishing Co., Easton, 1995).

Preferred pharmaceutical carriers depend upon the intended mode of administration of the active agent. Typical modes of administration include enteral (e.g., oral) or parenteral (e.g., subcutaneous, intramuscular, or intravenous intraperitoneal injection; or topical, transdermal, or transmucosal administration).

A "subject" of diagnosis or treatment is a mammal, including a human. Non-human animals subject to diagnosis or treatment include, for example, primates.

A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

"Short consensus repeat" ("SCR") refers to a polypeptide moiety having a secondary structure reflecting two disulfide bonds created by four cysteine residues in the polypeptide moiety. SCRs in various complement binding proteins are attached by short peptide moieties of about 4 amino acids. SCRs are unique in that the first and third cysteine residues are always disulfide linked to each other and the second and fourth residues are also always disulfide linked to each other.

"Graft" refers to any free (unattached) cell, tissue or organ for transplantation.

"Allograft" refers to a transplanted cell, tissue or organ derived from a different animal of the same species.

"Xenograft" refers to a transplanted cell, tissue or organ derived from an animal of a different species.

A protein "inhibits complement activation" if it decreases hemolysis in the $CH_{50}$ inhibition assay to a statistically significant degree (p>0.05). The $CH_{50}$ assay, also called the 50% hemolysis assay, is well known to immunologists. In general, the greater the degree of inhibition of complement activation, the less dilution of the serum necessary to achieve 50% lysis of the sheep red blood cells used in the assay. The assay is described in the Examples herein.

A "complement-mediated condition" is a pathological condition in which complement activation contributes in an observable or measurable way to the pathology of the condition. Many complement-mediated conditions are characterized by the destruction of cells through complement activation.

A "complement-inhibiting portion of SPICE" is a polypeptide fragment of SPICE that inhibits complement activation.

The term "sCR1" is used herein to denote a recombinantly engineered form of CR1, wherein the transmembrane region of CR1 has been removed, such that sCR1 is a soluble protein. sCR1 is available from T Cell Sciences (Cambridge, Mass.).

SPICE and SPICE-Related Polypeptides

The invention provides a protein that has not, until now, been provided in substantially pure form. The protein is a smallpox inhibitor of complement enzymes ("SPICE"). The invention also provides SPICE-related polypeptides that include a complement-inhibiting portion of SPICE. SPICE and SPICE-related proteins inhibit complement activation. Activation of complement can be inhibited by several molecular mechanisms. One mechanism is the acceleration of the decay of complement complexes. Another mechanism is through a cofactor activity that involves binding and inactivating complement proteins. Cofactor substrates of complement inhibitors include C3b and C4b.

As inhibitors of complement, SPICE and SPICE-related molecules are useful for the treatment of the many pathological conditions that are mediated by complement activation. Hyperacute rejection of transplanted tissue is a pathologic situation that is mediated by complement activation. It is a particularly attractive target of therapeutic intervention in the methods of the present invention.

SPICE and SPICE-related polypeptides can be produced recombinantly by expressing a polynucleotide encoding the polypeptide. Chemical synthesis of the molecule using currently available technologies is possible, but the method tends to be cumbersome.

SPICE

The amino acid sequence of SPICE is presented in FIG. 2 (SEQ ID NO:4) and can be described as follows: Referring to FIG. 2, a signal sequence extends from amino acid 1 to about amino acid 19. Four SCRs extend from about amino acid 20 to amino acid 263. Each SCR is characterized by four cysteine residues. The four cysteine residues form two disulfide bonds in the expressed protein. The boundaries of each SCR are best defined by the first and fourth cysteine residues in the sequence that form the disulfide bonds of the SCR. An invariant tryptophan residue is present between cysteine 3 and cysteine 4 of each SCR. SCR1 extends from amino acid 20 or 21 to amino acid 81. Both residues are cysteines that may be involved in disulfide bonding. SCR2 extends from amino acid 86 to amino acid 143. SCR3 extends from amino acid 148 to amino acid 201. SCR4 extends from amino acid 206 to amino acid 261. The SCRs include the complement binding locations of SPICE.

The exact positions of amino acids that bind these proteins have not yet been confirmed. However, they are expected to be located on exposed portions of the native molecule.

SPICE-related Polypeptides

The invention also provides SPICE-related polypeptides that inhibit complement activation. SPICE-related proteins are proteins other than full-length SPICE that comprise at least a complement-inhibiting portion of SPICE. A complement-inhibiting portion of SPICE includes, for example, the four SCRs of SPICE, e.g., from amino acid 20 or 21 to amino acid 261. SPICE-related proteins include fragments of SPICE and fusion proteins comprising a SPICE polypeptide moiety and a second peptide moiety, as well as larger multimeric molecules that include at least one polypeptide that comprises a complement-inhibiting portion of SPICE.

Fragments of SPICE

In one embodiment, the SPICE-related polypeptide is a polypeptide fragment of SPICE that includes a complement-inhibiting portion of SPICE. The signal sequence of SPICE, spanning amino acid 1 to about amino acid 19, is not necessary to confer complement inhibiting activity. Therefore, any portion of this sequence can be excluded in a SPICE fragment without eliminating inhibition of complement activation. Such fragments of SPICE are useful inhibitors of complement activation. Also, full-length SPICE and fragments of it have utility as polypeptide moieties in fusion proteins that provide other advantages.

Fusion Proteins Comprising a Complement-inhibiting Portion of SPICE

In another embodiment, the invention provides fusion polypeptides comparing at least a complement-inhibiting portion of SPICE and a second polypeptide. In such fusions, the second polypeptide can be fused to the amino-terminal end of the portion, the carboxy-terminal end of the portion or at both ends, so that the portion of SPICE is within a larger polypeptide. In a fusion protein, the second polypeptide can provide several different functions. It will be understood that the second polypeptide can provide more than one of these functions.

Fusions that Simplify Purification of SPICE

One function of the second polypeptide is to simplify purification of recombinant SPICE from a mixture, such as a cell homogenate or a supernatant. In such constructs, the second polypeptide is a moiety that has affinity for an affinity reagent that binds and captures the fusion protein, thereby isolating it from a mixture. In one embodiment, the second polypeptide comprises an epitope recognized by an antibody. In such cases, the antibody can be used on an affinity matrix to purify the fusion protein. In another embodiment, the second polypeptide is at least a portion of an immunoglobulin molecule, such as the Fc portion, that contains binding sites for protein A or protein G or that is recognized by an anti-heavy chain antibody. In another embodiment, the second polypeptide is a poly-His sequence that can be isolated on, for example, nickel-chelate affinity matrices, such as nickel-NTA resins.

Fusions that Extend the Half-life of the Polypeptide

Another function of the second polypeptide is to extend the half-life of the SPICE moiety in a subject to whom it is delivered. Many recombinant proteins have half lives in the circulatory system of a few minutes to hours. However, in therapeutic methods of inhibiting complement activation, a SPICE-containing polypeptide having a half-life of several days or weeks is more efficient to administer. Accordingly, the invention provides fusion proteins in which the second polypeptide moiety confers a half-life on the fusion protein of that is significantly greater (p>0.05) than full-length SPICE. In general, such moieties are polypeptide of at least about 200 amino acids. In one embodiment, the second polypeptide is an immunoglobulin heavy chain or a portion thereof. Such portions include at least two constant region domains or substantially all of the Fc portion of an immunoglobulin. Preferably, the SPICE portion is attached to the amino-terminus of the immunoglobulin molecule.

Fusion Proteins Adapted for Secretion from the Cell

Another embodiment is a fusion protein comprising a complement-inhibiting portion of SPICE and a polypeptide moiety that functions as a signal sequence to direct secretion of a recombinantly expressed protein from the cell. Such signal sequences are well known in the art. Signal sequences generally are hydrophobic. They can be adapted for use in prokaryotes or eukaryotes. Signal sequences can be those naturally cleaved by the cell, or can incorporate cleavage sites directed toward target proteases that remove the signal sequence from the protein. Note that putative full-length SPICE naturally possesses a signal sequence. This sequence can be used for a secretion function in other SPICE-related polypeptides.

Fusions that Render SPICE a Cell-surface Protein

Another embodiment is to express a complement-inhibiting portion of SPICE as a cell surface protein. Such fusion proteins comprise a complement-inhibiting portion of SPICE fused to a second polypeptide that comprises a transmembrane domain. The transmembrane domain functions to anchor the fusion protein in the cell membrane. Cells that bear a complement-inhibiting portion of SPICE on their surfaces are resistant to complement-mediated damage. Cells of xenografts, and, in particular, endothelial cells of blood vessels in xenografted organs, are subject to complement-mediated hyperacute rejection. Therefore, cells of such xenografts that are engineered to express on their surfaces a complement-inhibiting portion of SPICE are resistant to such rejection.

Generally, transmembrane regions are characterized by hydrophobic amino acid residues that fit the hydrophobic environment of the cell membrane. Such constructs can include, from the amino-terminus, a polypeptide moiety that functions as a signal sequence, a complement-inhibiting portion of SPICE, a transmembrane region and a cytoplasmic region. The transmembrane region can be selected from naturally occurring proteins or modified versions of them.

In one embodiment, the second polypeptide moiety comprises the transmembrane region of a cell surface complement receptor. Such proteins include, for example, CR1, CR2, DAF and MCP. However, transmembrane regions of other cell surface receptors also are useful. The include, for example, CD4, CD8, MHC Class I and II, LCL receptor.

Another method of anchoring a protein to a cell surface is by use of a lipid anchor, such as a GPI (glycosyl-phosphotidylinositol) structure.

Fusions that Provide SPICE Activities to Other Regulators of Complement Activation Several molecules are known as inhibitors of complement activation whose structure include short consensus repeats.

These include, for example, Factor H, C4bp, CR1, CR2, DAF, MCP and VCP. The complement-binding function of these molecules resides in the short consensus repeats. By adding a complement-inhibiting portion of SPICE to these molecules, or by replacing SCRs of these molecules with a complement-inhibiting portion of SPICE, new fusion molecules can be created having mixed functions of these molecules. More particularly, a complement-inhibiting portion of SPICE can be attached to a terminal SCR of a regulator of complement activation, can be inserted between any SCR in such a molecule, or can replace any number of SCRs in such a molecule.

The most common allotype of CR1 has 30 SCRs that include three groups of four SCRs (nos. 1–4, 8–11 and 15–18, counted from the amino terminus) that function in complement binding. CR1 has been produced in soluble form by eliminating the transmembrane region. In one embodiment of the invention, any or all of the three complement-binding sets of the four SCRs are replaced with a complement-inhibiting portion of SPICE.

CR2 has 15 or 16 SCRs. The two amino-terminal SCRs of this protein function in complement binding. Accordingly, these two amino-terminal SCRs of CR2 can be replaced with a complement-inhibiting portion of SPICE.

C4bp comprises seven identical chains of 8 SCRs bound together by a common protein. On or more amino-terminal SCRs not bound to the common protein in at least one chain can be replaced with a complement-inhibiting portion of SPICE. (See Pasek et al., WO 91/11461.)

Fusions that Provide Multimeric Versions of SPICE

In another embodiment, the SPICE-related protein contains a multimer of SPICE. That is, the protein can comprise a plurality of sets of the four SCRs from SPICE with between 1 to about 100 amino acids in between the sets to act as spacers between the sets. SPICE multimers include dimers, trimers and tetramers of complement-inhibiting portions of SPICE as well as those containing up to ten or more than ten copies of a complement-inhibiting portion of SPICE. Because they include a plurality of binding sites for complement, SPICE multimers are expected to have greater complement-inhibition activity than molecules including only a monomer of a SPICE complement-inhibiting portion.

Fusions that Provide a Targeting Function

Another function of the second polypeptide moiety is to provide a targeting function that targets the SPICE moiety to a location of interest. Important targets include locations in which complement is expected to be activated and result in tissue damage. Such locations include endothelial cell surfaces, especially of xenografts, sites of inflammation, and arthritic joints, neural tissues and renal glomerulus.

Polypeptide moieties that target particular locations include ligands for receptors at the location. Ligands include both binding partners for receptors, such as cell surface receptors, antibodies that specifically bind the target receptor and polypeptide agents that bind the target that have been identified from, for example, combinatorial libraries. For example, endothelial cells at sites of inflammation express E-selectin, P-selectin and VCAM1. Accordingly, the second polypeptide moiety can be a ligand of these molecules such as VLA4. Alternatively, the ligand could be an antibody specific for these cell surface proteins. In another embodiment, the fusion protein comprises a carboxy-terminal portion that includes an Fc domain and an amino-terminus that includes the complement-inhibiting portion of SPICE. Fc molecules are recognized by Fc receptors on cells. Some cells have Fc receptors that bind particular Fc molecules. For example, Fcε is recognized by high affinity Fc receptors on mast cells and by low affinity Fcε receptors (CD23) expressed in a broader tissue distribution. Fcγ is recognized by receptors on phagocytic cells. Therefore, by adding different Fc domains, one can target the SPICE molecule to different cell types.

The invention also provides multivalent constructs for targeting a complement-inhibiting portion of SPICE to a particular location. These constructs are multimeric molecules comprising a first polypeptide that includes at least a complement-inhibiting portion of SPICE and second polypeptide that includes a ligand for a target receptor. For example, the construct can be an "immuno-complement inhibitor." In one such construct, a complement-inhibiting portion of SPICE is fused to at least one chain of at least a portion of an immunoglobulin chain that comprises an antigen binding site. Preferably, the SPICE portion is attached at the carboxy-terminus of the molecule. In one embodiment, the SPICE portion is attached to at least an Fab region of an antibody. This includes (Fab)$_2$ regions or entire immunoglobulin. Preferably, the SPICE portion is attached to an immunoglobulin heavy chain.

In another construct, the SPICE portion replaces the variable region of one heavy-light chain dimer of an immunoglobulin. The construct need not include an entire immunoglobulin heavy chain. However, it should include a sufficient portion of the $CH_1$ and $CH_2$ portions to allow assembly of the molecule by disulfide bonding.

Variola RCA Chimeric Proteins

In another aspect, the invention provides variola-regulators of complement activation (RCA) chimeric proteins. The chimeric proteins of the invention comprise at least one SCR from SPICE (i.e., SCR2, SCR3 or SCR4) and at least one SCR from an RCA (e.g., CR1, CR2, C4bp, DAF, MCP, Factor H and VCP). The SCRs are selected so that the chimeric protein inhibits complement activation.

Because VCP and (as a result of the invention) SPICE both are now known to inhibit complement, the invention contemplates chimeric proteins in which the SCRs of SPICE and VCP are swapped to form chimeric protein having the SCR common to both molecules, on or two SCRs from SPICE and two or one SCRs from VCP, respectively. That is, the molecule could contain from SPICE SCR2, SCR3 or SCR4 alone, or SCR2 and SCR3, or SCR2 and SCR4 and/or SCR1, SCR2 and SCR3 in combination.

In another embodiment, the chimeric protein comprises at least a complement-inhibiting portion of SPICE and a series of SCRs from a regulator of complement activation that binds a complement protein (e.g., C1, C2, C3, C4, C5, C6, C7, C8, C9, their complexes or their reaction products) in the classical or alternate complement activation pathways.

Polynucleotides encoding such chimeras can be constructed by recombinant combination of SCR-encoding polynucleotides from the two molecules. Such proteins can be expressed conveniently by recombinant expression, as described herein.

Polynucleotides Encoding SPICE or SPICE-Related Polypeptides

The invention also provides recombinant polynucleotides that encode the SPICE or SPICE-related molecules of the invention. The proteins of the invention include at least a complement-inhibiting portion of SPICE. When a natural source of a target polynucleotide is available, the target can be isolated by amplification by, or example, PCR using primers directed to the nucleotide sequences flanking the target sequence. However, access to polynucleotides from the variola genome is restricted. Therefore, it was not possible to produce a polynucleotide from the variola genome that encoded SPICE. However, polynucleotides from the vaccinia genome encoding VCP are readily available from the American Type Culture Collection. SPICE and VCP differ at twelve amino acid locations, 11 of which are in the SCR2, SCR3 and SCR4, and one of which is in the signal sequence. By a process of site-directed mutagenesis we prepared a polynucleotide that encodes a complement-inhibiting, portion of SPICE, i.e., the four SCRs of SPICE, by introducing nucleotide substitutions into a polynucleotide derived from vaccinia and encoding VCP by site-directed mutagenesis.

Accordingly, the invention provide a recombinant polynucleotide comprising a nucleotide sequence encoding a SPICE or SPICE-related polypeptide that inhibits complement activation and is derived from vaccinia. The SPICE-related polypeptide includes at least a complement-inhibiting portion of SPICE (SEQ ID NO:4), i.e., at least four SCRs of SPICE. The nucleotide sequence comprises a mutated vaccinia VCP sequence of SEQ ID NO:1) encoding the portion of SPICE and substituted with codons encoding amino acid substitutions: Q96H, H117Y, S122Y, E127K, E139K, S150L, E163N, D197N, S212L, K233T, and K255Q (referring to SEQ ID NO:2). Any codon that encodes the SPICE amino acid can be substituted for the corresponding codon in the VCP nucleotide sequence. However, insofar as the polynucleotide of the invention is to be used for expression in mammalian systems, codons that are preferentially used by mammalian cells. The codons we used are such preferred codons. Preferred codons refers to those codons that, statistically, are the ones most commonly used to encode an amino acid in a specific species.

The invention also provides expression vectors, e.g., recombinant polynucleotide molecules comprising expression control sequences operatively linked to a nucleotide sequence encoding the target polypeptide. Expression vectors can be adapted for function in prokaryotes or eukaryotes by inclusion of appropriate promoters, replication sequences, markers, etc. for transcription and translation of mRNA. The construction of expression vectors and the expression of genes in transfected cells involves the use of molecular cloning techniques also well known in the art and are described for example, in Sambrook et al. (1989, Molecular Cloning, A Laboratory Manual, Cold Spring Harbor Laboratory, Cold Spring Harbor, N.Y.) and in Ausubel et al., (1994, Current Protocols in Molecular Biology, Current Protocols, a joint venture between Greene Publishing Associates, Inc. and John Wiley & Sons, Inc.). Useful promoters for such purposes include a metallothionine promoter, a constitutive adenovirusmajor late promoter, a dexamethasone-inducible MMTV promoter, a SV40 promoter, a MRP polIII promoter, a constitutive MPSV promoter, a tetracycline-inducible CMV promoter (such as the human immediate-early CMV promoter), and a constitutive CMV promoter. A plasmid useful for gene therapy can comprise other functional elements, such as selectable markers, identification regions, and other genes. Recombinant DNA expression plasmids can also be used to prepare the polynucleotides of the invention for delivery by means other than by gene therapy, although it may be more economical to make short oligonucleotides by in vitro chemical synthesis.

Methods of transfecting genes into mammalian cells, either in vivo or ex vivo, and obtaining their expression are well known to the art. These include, for example, transfecting cells with the nucleic acid by means of nucleic acid vectors, such as viral vectors (including, e.g., retroviral vectors, adenoviral vectors, adeno-associated viral vectors, hepatitis viral vectors, vaccinia viral vectors and herpes viral vectors), plasmid vectors, cosmid vectors, microencapsulation vectors (e.g., cationic or uncharged liposomal microspheres); microinjection; electroporation; chromosome transfer; calcium precipitation; or biolistic injection (e.g., attaching DNA to a particle, such as a gold bead, and propelling it into a cell). See also, for example, Goeddel (ed. 1990, Methods in Enzymology, vol. 185, Academic Press, Inc., San Diego, Calif.) or Kriegler (1990, Gene Transfer and Expression, A Laboratory Manual, Stockton Press, New York, N.Y.).

Expression vectors useful in the invention depend on their intended use. Such expression vectors must, of course, contain expression and replication signals compatible with the host cell. Expression vectors useful for expressing the protein of the invention include viral vectors such as alpha viruses, retroviruses, adenoviruses and adeno-associated viruses, plasmid vectors, baculovirus vectors, cosmids, liposomes and the like. Viral and plasmid vectors are preferred for transfecting mammalian cells. The expression vectors pcDNA1 and pcDNA3 (Invitrogen, San Diego, Calif.), in which the expression control sequence comprises the CMV promoter, provides good rates of transfection and expression. Adeno-associated viral vectors are useful in the gene therapy methods of the invention.

The construct can also contain a tag to simplify isolation of the protein. For example, a polyhistidine tag of, e.g., six histidine residues, can be incorporated at the amino terminal end of the protein. The polyhistidine tag allows convenient isolation of the protein in a single step by nickel-chelate chromatography.

In another embodiment, endogenous genes are transcribed by operatively linking them to expression control sequences supplied endogenously that recombine with genomic DNA. In one method, one provides the cell with a recombinant polynucleotide containing a targeting sequence, which permits homologous recombination into the genome upstream of the transcriptional start site of target gene; the expression control sequences; an exon of the target gene; and an unpaired splice-donor site which pairs with a splice acceptor in the target gene. Such methods are discussed in Treco et al., WO 94/12650; Treco et al., WO 95/31560 and Treco et al., WO 96/29411.

The invention also provides recombinant cells comprising an expression vector for expression of the nucleotide sequences encoding a polypeptide of the invention. Host cells can be selected for high levels of expression in order to purify the protein. Mammalian cells are preferred for this purpose, but prokaryotic cells, such as *E. coli*, and eukaryotic cells such as insect cells, also are useful. The cell can be, e.g., a recombinant cell in culture, a cell ex vivo or a non-human cell in vivo.

Methods of Inhibiting Complement Activation

Complement activation occurs in systems in vitro, ex vivo and in vivo. In vitro, complement activation can occur in cell cultures containing mammalian blood serum. Ex vivo, complement activation can occur in cells and tissues marked for transfusion (e.g., blood) or transplantation (e.g., allograft or xenograft cells, tissues or organs). In vivo, complement activation is associated with a number of pathological conditions. The invention provides methods of inhibiting complement activation in vitro, ex vivo or in vivo involving exposing complement to a protein inhibitor of complement activation of the invention (e.g., SPICE, a SPICE-related protein or a SPICE-RCA chimeric protein) in an amount sufficient to inhibit complement activation. The methods of the invention involve contacting cells in vitro or ex vivo with a protein inhibitor of complement of the invention, administering a protein inhibitor of complement of the invention to a subject for the treatment of a complement-mediated condition, or providing cells with a recombinant polynucleotide that expresses a protein inhibitor of complement of the invention.

Pharmaceutical compositions

Certain methods of the invention involve administering a protein inhibitor of complement of the invention to a human subject, either by direct administration to the subject or by administration to cells, tissues or organs ex vivo before transplantation or transfusion. In these cases, the protein generally is administered in the form of a pharmaceutical composition. The pharmaceutical composition comprises a pharmaceutically acceptable carrier and an amount of a protein inhibitor of complement of the invention effective to inhibit complement activation in the system (i.e., a "pharmacologically effective amount"). The pharmaceutical compositions of the invention generally contain about 10 µg/ml to about 1000 mg/ml of the protein and, more generally, about 1 mg/ml to about 100 mg/ml. In one embodiment, the pharmaceutical composition of the invention is a unit dosage form comprising about 10 µg to about 1000 mg of the protein, generally about 10 µg to about 100 mg.

In another embodiment of the invention, the pharmaceutical composition is a perfusion solution for perfusing cells, tissues or organs before transplantation. In perfusion solutions the pharmaceutically acceptable carrier generally comprises saline or ringer's lactate.

In another embodiment, the invention provides a kit comprising a pharmaceutical composition of the invention and a label instructing its use in treating complement-mediated conditions.

The invention also includes a kit comprising the composition of the invention and an instructional material which describes adventitially administering the composition to a cell or a tissue of a mammal. In another embodiment, this kit comprises a (preferably sterile) solvent suitable for dissolving or suspending the composition of the invention prior to administering the compound to the mammal.

As used herein, an "instructional material" includes a publication, a recording, a diagram, or any other medium of expression which can be used to communicate the usefulness of the composition of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container which contains the composition of the invention or be shipped together with a container which contains the composition. Alternatively, the instructional material may be shipped separately from the container with the intention that the instructional material and the composition be used cooperatively by the recipient.

Methods of Inhibiting Complement Activation in the Treatment of Complement-Mediated Conditions The invention provides methods for the prophylactic or therapeutic treatment of complement-mediated conditions. Complement-mediated conditions include, for example: (1) those involving widespread cellular destruction (e.g., hyperacute allograft and xenograft rejection, hemodialysis disorders, interleukin-2-induced toxicity during IL-2 therapy), (2) hematologic malignancies, (3) post ischemic reperfusion conditions (e.g., myocardial infarction, bowel ischemia reperfusion injury, balloon angioplasty and post pump syndrome in cardiopulmonary bypass), (4) inflammatory disorders (e.g., burns and frostbite), (6) autoimmune diseases (e.g., rheumatoid arthritis, systemic lupus erythematosus, multiple sclerosis and myasthenia gravis), (7) immune system disorders (e.g., proliferative nephritis, glomerulonephritis and hemolytic anemia), (8) neurological disorders (e.g., Guillain Barre Syndrome, stroke, traumatic brain injury, Alzheimer's disease and Parkinson's disease), (9) infections (e.g., sepsis) and (10) complement activation caused by artificial surfaces (e.g., ventricular assist devices and dialysis membranes).

Methods of inhibiting complement activation in a subject in the treatment of complement-mediated conditions involves administering to the subject, a pharmacologically effective amount of a protein inhibitor of complement of the invention. These proteins can be administered by any route that gives it access to the target tissue or organ. Accordingly, the protein can be administered in the form of a pharmaceutical composition. This includes, for example, aqueous solutions for enteral, parenteral or transmucosal administration, e.g., for intravenous administration, as tonics and administration to mucous or other membranes as, for example, nose or eye drops; solid and other non-aqueous compositions for enteral or transdermal delivery, e.g., as pills, tablets, powders or capsules; transdermal or transmucosal delivery systems for topical administration, and aerosols or mists for delivery by inhalation. An advantage of delivery by a mode that is easy to administer, e.g., enteral or by intravenous or intramuscular injection is that such modes mimic possible modes of delivery should the agent be formulated as a pharmaceutical.

Single or multiple administrations of the compositions can be carried out with dose levels and pattern being selected by the treating physician. In any event, the pharmaceutical formulations should provide a quantity of a compound of the invention sufficient to treat the patient effectively.

The total effective amount of a compound of the present invention can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a compound of the present invention required to obtain an effective dose in a subject depends on many factors including the age and general health of the subject, the route of administration, the number of treatments to be administered and the judgment of the prescribing physician. In view of these factors, the skilled artisan would adjust the dose so as to provide an effective dose for a particular use. Nevertheless, a pharmacologically effective dose is about 10 µg/kg to about 1000 mg/kg (preferably about 10 mg/kg to about 100 mg/kg) administered in serial doses timed to the half-life of the protein.

In certain conditions complement activation is localized to particular body location. For example, in rheumatoid arthritis, inflammation occurs at the joints. In such cases, the complement inhibitor can be delivered directly to the affected location. For example, in rheumatoid arthritis, the inhibitor can be delivered by intra-articular injection.

Methods of Inhibiting Hyperacute Reaction of Allografts or Xenografts

The complement inhibitors of the invention are particularly useful in methods for inhibiting hyperacute rejection of allografts or xenografts.

In one method of the invention, a graft is prepared for transplantation exposing it to a complement inhibitor of the invention. For example, after an organ is removed from the donor and before transplantation into the recipient, the organ can be washed with a solution comprising the complement inhibitor and its blood vessels can be perfused with the solution.

Upon transplantation of the graft into the recipient, the recipient can be administered a complement inhibitor of the invention to inhibit rejection of the donated material.

In another method of the invention, hyperacute rejection is inhibited by using as donor material, grafts from animal hosts made transgenic for, and expressing a protein inhibitor of complement of the invention. In one embodiment, these transgenic animals express the complement inhibitor as cell surface proteins on their endothelial surfaces, at least. The complement inhibitors protect the endothelial cells from complement-mediated damage. Alternatively, the graft cells can secrete the complement inhibitors, so that the environment around the cells inhibits complement activation.

Methods Involving Gene Therapy

This method also provides gene therapy methods for inhibiting complement activation. In these methods, cells of the subject are transfected, in vivo or ex vivo with a vector comprising a complement inhibitor of the invention. The vector may be an expression vector, or may be designed to integrate into the cell's genome so as to operatively link the polynucleotide encoding the complement inhibitor to an expression control sequence. The resulting cells express the complement inhibitor thereby providing a therapeutic agent to the subject.

In one embodiment, the genes are introduced into cells of the individual in vivo by means of expression vectors. In another embodiment, the genes are introduced into cells ex vivo, and transfected cells that express and secrete the protein are administered to the subject.

Viral vectors are particularly useful for gene therapy. Methods for constructing and using viral vectors are known in the art and are reviewed, for example, in Miller and Rosman (1992, Biotechniques 7:980–990). Adenoviruses, adeno-associated viruses and retroviruses all have been used as vectors in gene therapy. Dosages include about of $10^7$ to $10^{13}$ particles of viral vector per ml of carrier. The volume administered can be selected by the practitioner. According to one embodiment of the invention, approximately $10^{10}$ vectors suspended in about 1 ml of sterile PBS constitute an effective amount.

In a method of treating arthritis, a vector for gene therapy is administered to the intraarticular space in order to transfect cells there and express the complement inhibitor.

Methods of Inhibiting Complement Activation in Blood Loops

Complement can be activated in extra-corporeal blood loops. Accordingly, surfaces of these machines that are exposed to blood can be coated with a complement inhibitor of the invention. Methods of attaching proteins to such surfaces are well known in the art.

Methods of Inhibiting Complement Activation in a Blood Product

Blood and blood products are subject to damage by complement activation. Accordingly, the invention provides methods for inhibiting complement activation in a blood product by contacting the blood product with a protein inhibitor of complement activation of the invention. Blood products include, for example, whole blood, red cell concentrates, platelet concentrates, leukocyte concentrates, blood cell proteins, blood plasma protein fractions, purified blood proteins, serum, a blood plasma fractionation precipitate, a blood plasma fractionation supernatant, cryoprecipitate, cryosupernatant, purified antibodies or portion or derivative thereof.

The invention also provides a blood product treated with a protein inhibitor of complement of the invention. The product comprises an amount of the protein effective to inhibit complement activation.

Transgenic Animals Expressing SPICE-Related Polypeptides and Their Organs

The invention also provides non-human mammals transgenic for a protein inhibitor of complement of the invention. As used herein, "animal transgenic for SPICE or a SPICE-related protein" refers to an animal, in particular a mammal, whose germ cells (i.e., oocytes or sperm), at least, comprise a recombinant polynucleotide comprising expression control sequences operatively linked to a nucleotide sequence encoding the protein inhibitor of complement. Such animals are useful, for example, as models in the study of complement activation. Such animals also are useful as organ donors in xenograft transplants. Particularly useful transgenic mammals of the invention include primates, such as baboons, and domesticated farm animals, such as pigs or sheep.

The transgenic animals of the invention can express any of the proteins of the invention. SPICE- related proteins having polypeptide moieties that anchor them to the cell surface are especially attractive. Such molecules include those in which the complement-inhibiting portion of SPICE is attached to a portion of CR1, CR2, DAF or MCP. Alternatively, the protein maybe selected to be secreted from the cell. Such versions are useful to introduce the protein inhibitor of complement into the interstitial space.

In hyperacute rejection, xenograft tissues are subject to complement-mediated destruction. Because complement is carried by the blood, tissue surfaces exposed to are especially vulnerable. Endothelial cell surfaces in these organs, such as blood vessels, frequently show the most severe damage. It is useful for all cells of a transgenic animal whose organs are to be transplanted to express SPICE or a SPICE-related protein of the invention. However, because they are most exposed to complement, it is particularly important for endothelial cells, as well as underlying and adjacent tissues, of these animals to express the proteins of the invention. Such animals can be created by transgenic introduction of a recombinant polynucleotide having an expression control sequence operative in endothelial cells operatively linked to the protein. Alternatively, in any creation of transgenic animals, some are expected to show a pattern of expression that includes endothelial cells. Such animals can be identified by inspection of their tissues.

In another embodiment the invention provides transgenic animals that express the protein in the mammary gland. For this purpose, a transcription promoter from a milk protein gene is used. Milk protein genes include those genes encoding the caseins (see U.S. Pat. No. 5,304,489), β-lactoglobulin, α-lactalbumin, and whey acidic protein. The β-lactoglobulin (BLG) promoter is preferred. See also Whitelaw et al. (1992, Biochem J. 286:31–39) and (WO 95/23868).

In one embodiment, the expression control sequences are not naturally found operatively linked to a protein inhibitor of complement. In one embodiment, the recombinant polynucleotide comprises a non-native SPICE or a SPICE-related protein coding sequence, i.e., a SPICE or a SPICE-related protein sequence that the species does not produce in nature. In another embodiment, the expression control sequences are non-native expression control sequences introduced into the germ cells so as to recombine with the naturally occurring gene and control its expression.

The transgenic animals of the invention are produced, for example, by introducing the recombinant polynucleotide molecule into a fertilized egg or embryonic stem (ES) cell, typically by microinjection, electroporation, lipofection, particle-mediated gene transfer. The transgenic animals express the heterologous nucleotide sequence in tissues depending upon whether the promoter is inducible by a signal to the cell, or is constitutive. Transgenic animals can be bred with non-transgenic animals to produce transgenic animals with mixed characteristics.

Organs, tissues and cells from the transgenic non-animals of the invention are useful in xenografts because the protein inhibitor of complement they express render them resistant to complement-mediated damage. Accordingly, the invention provides such organs and tissues, isolated from a transgenic animal.

The invention is now described with reference to the following examples. These examples are provided for the purpose of illustration only and the invention should in no way be construed as being limited to these examples but rather should be construed to encompass any and all variations which become evident as a result of the teaching provided herein.

EXAMPLES

Generation of pRe1SPICE

The nucleotide and protein sequences of the entire genome of the variola major virus (strain Bangladesh-1975) were originally published in 1993 (Massung et al., 1993, Nature 366:748–751). The protein sequence published was:

MKVERVTFLTLLGIGCVLSCCTIP-SRPINMKFKNSVETDANANYNIGDTIEYLCL PGY-RKQKMGPIYAKCTGTGWTLFN-QCIKRRCPSPRDIDNGHLDIGGVDFGSSIT YSCNSGYYLIGEYKSYCKLGSTGSMVWN-PKAPICESVKCQLPPSISNGRHNGY NDFYTDGSV-VTYSCNSGYSLIGNSGVLCSGGEWSN-PPTCQIVKCPHPTILNGYL SSGFKRSYSYNDNVDFTCK-YGYKLSGSSSSTCSPGNTWQPELPKCVR (SEQ ID NO:4).

This was translated from the nucleotide sequence:

```
atgaaggtgg agagagtgac gttcctgaca ttgttgcgaa taggatgcgt   50 (SEQ ID NO:3)
tctatcatgc tgtactattc cgtcacgacc cattaatatg aaatttaaga  100
atagtgtgga gactgatgct aatgctaatt acaacatagg agacactata  150
gaatatctat gtctacctgg atacagaaag caaaaaatgg gacctatata  200
tgctaaatgt acaggtactg gatggacact ctttaatcaa tgtattaaac  250
ggagatgccc gtcgcctcga gatatcgata atggccatct tgatattggc  300
ggagtagact ttggctctag tataacgtac tcttgtaata gcggatatta  350
tttgattggt gaatataaat cgtattgtaa attaggatct actggatcta  400
tggtatgaa  tcccaaggca cctatttgcg aatctgttaa atgccaatta  450
cctccatcta tatccaacgg aagacataac ggatataatg atttttatac  500
cgatggaagc gttgtaactt atagttgcaa tagtggatat tcgttgattg  550
gtaactctgg tgtcctgtgt tcaggaggag aatggtctaa tccacccacg  600
tgtcagattg ttaaatgtcc acatcctaca atattaaacg gatacttgtc  650
tagcgggttt aaaagatcat attcgtataa tgacaatgta gactttacgt  700
gcaagtacgg atataaacta tctggttcct catcatctac ttgctctcca  750
ggaaatacat ggcaaccgga acttccaaaa tgtgtacgc
```

Due to the tight restrictions on the availability of the smallpox virus and genome, the recombinant form of SPICE was generated through site-directed mutagenesis of the vaccinia homologue, vaccinia virus complement control protein (VCP). The amino acid sequences of VCP and SPICE are compared in FIG. 4.

The nucleotide sequence that was used to generate SPICE is listed in FIG. 3. This sequence is not identical to that published by Massung, et al. (supra) since VCP was used as a template from which to create SPICE. However, once translated, the SPICE protein sequence from amino acid 20-263 is identical to that published by Massung et al. (supra).

Initially, the VCP sequence from pRe1VCP1234 flanked by the restriction enzyme sites of PspA1 and Xho1 was subcloned into the identical sites of the polylinker region of pBluescript®IIKS (+). The mutations were performed using Quik Change™ (Stratagene, La Jolla, Calif.) and the novel nucleotide sequence was established to be correct. The primers used to create each of the 11 amino acid changes are listed below. In total, 13 nucleotides were mutated to generate SPICE.

Sets of Primers used to generate the nucleotide changes are as follows. Amino acid and nucleotide substitutions are given based on their number position in the sequence, beginning with the initial methionine amino acid and codon. Thus, Q96H indicates that Q at amino acid position 96 was substituted with H. A288T indicates that A at nucleotide position 229 was substituted with T.

1. Amino Acid change: Q96H Nucleotide change: A288T 5' CGATAATGGC CATCTTGAT ATTGGTGG 3' (SEQ ID NO:7) 3' GCTATTACCG. GTAGAACTA TAACCACC 5' (SEQ ID NO:8)
2. Amino Acid change: H117Y Nucleotide change: C349T 5' CGTACTCTTG TAATAGCGGA TATTATTTG ATCGGTG 3 (SEQ ID NO:9) 3' GCATGAGAAC ATTATCGCCT ATAATAAAC TAGCCAC 5 (SEQ ID NO:10)
3. Amino Acid change: S122Y Nucleotide change: C365A 5' GATCGGTGAA TATAAATC GTATTG 3' (SEQ ID NO: 1) 3' CTAGCCACTT ATATTTAG CATAAC 5' (SEQ ID NO:12)
4. Amino Acid change: E127K Nucleotide change: G379A 5' AAATCGTATT GTAAATTAG GATCTACTGG ATCTATGG 3' (SEQ ID NO:13) 3' TTTAGCATAA CATTTAATC CTAGATGACC TAGATACC 5' (SEQ ID NO: 14)
5. Amino Acid change: E139K Nucleotide change: G415A 5' GGTATGGAAT CCCAAGGCA CCTATTTGT G 3' (SEQ ID NO:15) 3' CCATACCTTA GGGTFCCGT GGATAAACA C 5' (SEQ ID NO:16)
6. Amino Acid change: S105L Nucleotide change: C449T and C450T 5' CTGTTAAATG CCAATTGCC TCCATC 3' (SEQ ID NO: 17) 3' GACAATTTAC GGTTAACGG AGGTAG 5' (SEQ ID NO:18)
7. Amino Acid change: F163N Nucleotide change: G487A and G489T 5' GACATAACGG ATACAATGAT TTTTATACCG ATGGG 3' (SEQ ID NO: 19) 3' CTGTATTGCC TATGTTACTA AAAATATGGC TACCC 5' (SEQ ID NO:20)
8. Amino Acid change: D197N Nucleotide change: G589A 5' GAATGGTCCA ATCCACCCA CGTGTC 3' (SEQ ID NO:21) 3' CTTACCAGGT TAGGTGGGT GCACAG 5' (SEQ ID NO:22)
9. Amino Acid change: S212L Nucleotide change: CG35T 5' GTCCACATCC TACAATATTA AACGGATACT TGTCTAGGGG G 3' (SEQ ID NO:23) 3' CAGGTGTAGG ATGTTATAAT TTGCCTATGA ACAGATCGCC C 5' (SEQ ID NO:24
10. Amino Acid change: K233T Nucleotide change: A698C 5' CGACAATGTA GACTTTACGT GCAAGTACGG 3' (SEQ ID NO:25) 3' GCTGTTACAT CTGAAATGCA CGTTCATGCC 5' (SEQ ID NO:26)
11. Amino Acid change: K255Q Nucleotide change: A763C 5' GGAAATACAT GGCAGCCGG AACTTC 3' (SEQ ID NO:27) 3' CCTTTATGTA CCGTCGGCC TTGAAG 5' (SEQ ID NO:28)

Generation of SPICEFc

The fusion protein SPICEFc was designed so as to contain the full length SPICE protein sequence fused to the Fc domain of mouse IgG2a. Prior to creating the two plasmids that contained the sequence for SPICEFc, SPICE was cloned out of Bluescript and subcloned into the CDM8 expression vector containing the sequence for SCR3–15 of Complement Receptor Type 2 (CR2) to create pRe1SPICE.CR2.

The SPICE sequence flanked by the PspA1 and Xho1 sites was subcloned into pRe1VCP1234 in place of VCP to create pRe1SPICE.CR2 (FIG. 3a). The SPICE sequence was confirmed using the Applied Biosystems Inc Stretch sequencer (Perkin Elmer, Foster City, Calif.)(DNA Sequencing Facility, University of Pennsylvania, Philadelphia, Pa.). The oligonucleotides used to sequence the plasmid pRe1SPICE.cr2 are listed below:

1. CR2.29–80 (from the 5' untranslated region of CR2) (Martin et al., 1991, J.Exp. Med. 174:1299–1311): AGG AAT TCC GCC GCG GGG GCT TC (SEQ ID NO:29)
2. V289–310 (from the VCP sequence at position 238–259): CAA TGT ATT AAA CGG AGA TGC (SEQ ID NO:30)
3. V618–639 (from the VCP sequence at position 568–588): TGT TCA GGA GGA GAA TGG TCC (SEQ ID NO:31)
4. V639–618 (antisense, from the VCP sequence at position 588–568): GGA CCA TTC TCC TCC TGA ACA (SEQ ID NO:32)
5. V310–289 (antisense, from the VCP sequence at position 259–238): GCA TCT CCG TTT AAT ACA TTG (SEQ ID NO:33
6. CR2.639–616 (antisense, from the CR2 sequence at position 639–618) (Martin et al., J. Exp. Med. 1991, 174:1299–1311): CTG TAA GTC ACA GAC AAT CCT (SEQ ID NO:34)

SPICEFc was created using two different plasmids, pApHygSPICEFc and pcDNA3SPICEFc. Plasmid pApHyg is a eukaryotic expression vector created by cloning the 3.9 Kb BamHI-Pvul restriction fragment encoding Hygromycin B resistance from plasmid pHyg into plasmid pApM8. Plasmid pcisCD19Fc encodes a fusion protein that consists of the extracellular domain of human CD19 fused to the Fc domain of mouse IgG2a. A fragment encoding the Fc domain was removed from pcis CD19Tc by restriction with XhoI and XbaI, a HindIII-XhoI fragment encoding VCP was removed from pRe1VCP 1234, and the two fragments were ligated with ApHyg that had been restricted by HindIII and XbaI to create pApHygVCPFc. A BamHI-XbaI fragment encoding the VCPFc fusion protein was removed and ligated to BamHI-XbaI-digested pcDNA3 (Invitrogen, San Diego, Calif.), creating pcDNA3VCPFc.

The SPICE sequence flanked by HindIII and XhoI was subcloned into pApHygVCPFc and the sequence encoding VCP was removed using the same restriction enzymes, thus creating pApHygSBFc (FIG. 5b). Thereafter, SPICE flanked by BamHI and XhoI was subcloned into pcDNA3VCPFc in place of the VCP sequence (using the same restriction enzymes), creating pcDNA3SPICEFc (FIG. 5c).

293T cells grown in complete DMEM (supplemented with L-glucose at 4500 mg/l, 2 mM glutamine (Life Technologies, Gaithersburg, Md.), penicillin (100 U/ml) and streptomycin (100 μg/ml) (P/S) (Life Technologies) and with 10% fetal bovine serum with ultralow bovine IgG (Life Technologies)), were transiently transfected using a calcium phosphate technique (adapted from Ausubel) and induced with 10 mM butyric acid (Sigma, St. Louis, Mo.) 12–24 hours after transfection. Culture supernatant was harvested 48 hours after transfection and immunoglobulin fraction precipitated at 4° C. for 8–12 hours using sepharose CL-4B protein A beads (Pharmacia, Uppsala, Sweden). Beads were collected by centrifugation and washed with phosphate buffered saline (PBS). SPICEFc was eluted with 0.2 M glycine pH 2.7, neutralized with Tris-HCl pH 9.0, dialyzed against PBS and concentrated in a centricon-10 or centricon-10 concentrator (Amicon, Beverly, Mass.). Final protein concentration was evaluated using spectrophotometric readings at 280 nm. The size and purity of SPICEFc were evaluated by 10% SDS-PAGE using the Laemmli discontinuous buffer system (FIG. 6a). A single band was observed with relative electrophoretic mobility consistent with the expected size of 55 kD. SPICEFc ran slightly faster than the VCPFc protein, purified in the same fashion.

Gels were transferred onto nitrocellulose paper and western blot technique was used to identify the protein either directly using anti-mouse Fc-peroxidase conjugated mAb (Jackson Immunoresearch Laboratories, West Grove, Pa.) or indirectly using mouse anti-VCPFc polyclonal primary antibodies (generated in mice against VCPFc at the monoclonal antibody facility of the University of Pittsburgh) and biotin labeled goat anti-mouse IgG (Sigma), followed by avidin-peroxidase. Western blots were developed using TMB ™ Membrane Peroxidase Substrate System (Kirkegaard and Perry Laboratory, Gaithersburg, Md.). Bands were compared using mouse and human CTLA4Ig, rat IgG, and bovine IgG as controls (FIG. 6b).

Inhibition of Complement

The $CH_{50}$ assay was adapted from Current Protocols in Immunology (John Wiley and Son, New York, N.Y.). Human serum (used as a source of human complement) (50 $\mu$l) was added to the top row of 96 well round bottom polypropylene plates (catalogue number 3790; Costar, Cambridge, Mass.) and 25 $\mu$l were serially diluted with PBS down each column of wells. An equivalent volume (25 $\mu$l) of the respective complement inhibitor or control protein (at equivalent concentrations) were dispensed into each well. All experiments were performed on ice. Antibody coated sheep erythrocytes (EAs) (Sigma) were washed in gelatin veronal buffer with calcium and magnesium (GVB++) (Sigma) and were resuspended in $1\times10^8$ cells/ml. 50 $\mu$l volumes of the EAs were added to each well. The contents of the wells were mixed in the plate and incubated at 37° C. on a rocking platform. 180 $\mu$l of ice cold normal saline were added to each well. The plates were centrifuged at 2500 RPMs for 5 minutes. Supernatants from each well (100 $\mu$l) were transferred into a flat bottom plate.

Control wells with background lysis contained no protein and the volume was replaced with PBS. Control wells for maximum obtainable lysis contained $H_2O$ instead of PBS and $H_2O$ was added in lieu of normal saline after the 60 minute incubation. The percentage of hemolysis was calculated by reading for hemoglobin release. Absorbance was read at 405 mn. Values were plotted. (FIGS. 7a, 7b, and 7c).

The $CH_{50}$ of sheep erythrocytes was determined to be significantly inhibited by SPICEFc, but not by other proteins that contained the same IgG2a Fc moiety, e.g. mouse CTLA4Ig (Finck et al., 1994, Science 265:1225–1227.) or mouse gamma-globulin.

SPICEFc and VCPFc Exhibit Species Preference in Complement Inhibition

Complement was obtained form a variety of different species of mammals, including human, baboon, dog and rabbit. Complement inhibition assays were performed as described herein, and it was discovered that the $CH_{50}$ of sheep erythrocytes was differentially affect by SPICEFc and VCPFc, depending on the species from which the complement was derived. For example, when compared with each other, SPICEFc was capable of inhibiting primate (human and baboon) complement activation better than the inhibition of primate complement activation by VCPFc. Conversely, VCPFc was capable of inhibiting non-primate (dog or rabbit) complement activation better than the inhibition of non-primate complement activation by SPICEFc. The optical densities of wells of 96 well plates containing different serum concentrations, with or without added protein, were read and plotted in FIGS. 8A–D.

The experiments whose results are presented in FIG. 8 were conducted as follows: Inhibition of the classical complement pathway was assessed by incubating 50 $\mu$l of antibody-coated sheep erythrocytes (EAs), at a concentration of $1\times10^9$ cells/ml in GVB++, 25 $\mu$l of different concentrations of human complement (as human serum, diluted in GVB++), and 25 $\mu$l of either different complementary regulatory proteins (i.e., SPICEFc, VCPFc, or soluble CR1 (sCR1)) diluted in PBS, or a control solution comprising PBS or mouse gamma globulin. The reaction mixture was incubated at 37° C. for one hour. The reaction was stopped by adding 180 $\mu$l of ice cold PBS, followed by centrifugation. The percent lysis was determined by measuring the optical density of 100 $\mu$l of supernatant at 405 nm. Maximum lysis was determined by substituting serum with Triton X-100. Background lysis was determined using heat-inactivated serum having an optical density of below 0.8 nm at all times. Mouse gamma globulin served as a control for the Fc portion of the fusion molecule. SPICEFc and sCR1 inhibited activation of both human and baboon complement. Conversely, VCPFc inhibited dog and rabbit complement activation to a greater extent than inhibition of human or baboon complement by this compound.

References

The references listed herein provide technical information of a general nature related to the present invention.

Ahearn et al., 1996, Immunity 4:251–262, 1996.
Bouter et al., 1973, Prog. Med. Virol. 16:86–108.
Croix et al., 1996, J. Exp. Med. 183:1857–1864.
Finck et al., 1994, Science 265:1225–1227.
Freed et al., 1972, Am. J. Med. 52:411–420.
Fulginiti et al., 1968, Birth Defects 4:129–145.
Hebell et al., 1991, Science 254:102–105.
Karp et al., 1996, Science 273:228–231.
Kotwal et al., 1990, Science 250:827–830.
Kotwal et al., 1988, Nature (Lond.). 335:176–178.
Massung et al., 1993, Nature 366 (6457), 748–751.
Payne, 1980, J. Gen. Virol. 50:89–100.

The disclosures of each and every patent, patent application, and publication cited herein are hereby incorporated herein by reference in their entirety.

While the invention has been disclosed with reference to specific embodiments, it is apparent that other embodiments and variations of the invention may be devised by others skilled in the art without departing from the true spirit and scope of the invention. The appended claims are intended to be construed to include all such embodiments and equivalent variations.

What is claimed is:

1. A SPICE-related fusion protein comprising at least one polypeptide moiety attached to at least a complement-inhibiting portion of smallpox inhibitor of complement enzymes (SPICE) protein (SEQ ID. NO:4), said portion including four short consensus repeats (SCRs) of SPICE, wherein said protein inhibits complement activation.

2. The fusion protein of claim 1, wherein said polypeptide moiety increases the half-life of the protein in the human circulatory system to at least about two days.

3. The fusion protein of claim 1, wherein said polypeptide moiety comprises a signal sequence that causes secretion of said protein from a cell upon expression of said protein in said cell.

4. The fusion protein of claim 1, wherein said polypeptide moiety comprises a transmembrane region that attaches said protein as expressed to a cell surface.

5. The fusion protein of claim 1, which comprises a SPICE multimer, wherein the polypeptide moiety comprises at least one complement-inhibiting portion of SPICE.

6. The fusion protein of claim 1, wherein said polypeptide moiety comprises a ligand that specifically binds a target receptor.

7. A pharmaceutical composition comprising a pharmaceutically acceptable carrier and a protein that inhibits complement activation in an amount effective to inhibit human complement activation, wherein said protein consist of
   a) smallpox inhibitor of complement enzymes (SPICE) protein (SEQ ID NO:4),
   b) a fragment of SPICE, said fragment comprising at least a complement-inhibiting portion of SPICE, said portion including four short consensus repeats (SCRs) of SPICE, wherein said protein inhibits complement activation, and
   c) a SPICE-related fusion protein comprising at least one polypeptide moiety attached to at least a complement-inhibiting portion of SPICE protein (SEQ ID NO:4), said portion including four SCRs of SPICE.

8. The pharmaceutical composition of claim 7 suitable for use as a perfusion solution of mammalian tissues maintained ex vivo.

9. A method of inhibiting complement activation comprising exposing complement to a protein that inhibits complement activation in an amount effective to inhibit complement activation, wherein said protein consist of
   a) smallpox inhibitor of complement enzymes (SPICE) protein (SEQ ID NO:4),
   b) a fragment of SPICE, said fragment comprising at least a complement-inhibiting portion of SPICE, said portion including four short consensus repeats (SCRs) of SPICE, wherein said protein inhibits complement activation, and
   c) a SPICE-related fusion protein comprising at least one polypeptide moiety attached to at least a complement-inhibiting portion of SPICE protein (SEQ ID NO:4), said portion including four SCRs of SPICE.

10. The method of claim 9 for the prophylactic or therapeutic treatment of a complement-mediated condition in a human subject, said method comprising the step of administering a pharmacologically effective amount of said protein inhibitor of complement to said subject.

11. The method of claim 10, wherein said complement-mediated condition is selected from the group consisting of hyperacute rejection, an inflammatory disorder and a post-ischemic reperfusion condition.

12. The method of claim 10, wherein said step of administering comprises administering a vector comprising a recombinant polynucleotide encoding said protein inhibitor of complement, wherein said vector transfects cells of the subject and said cells express said protein inhibitor of complement.

13. A method of inhibiting complement activation in blood in an extracorporeal blood loop, said method comprising the step of coating the surface of said blood loop that is exposed to blood with a protein that inhibits compliment activation, wherein said protein consist of
   a) smallpox inhibitor of complement enzymes (SPICE) protein (SEQ ID NO:4),
   b) a fragment of SPICE, said fragment comprising at least a complement-inhibiting portion of SPICE, said portion including four short consensus repeats (SCRs) of SPICE, wherein said protein inhibits complement activation, and
   c) a SPICE-related fusion protein comprising at least one polypeptide moiety attached to at least a complement-inhibiting portion of SPICE protein (SEQ ID NO:4), said portion including four SCRs of SPICE.

14. A blood product comprising at least a serum fraction of human blood and an amount of a protein that inhibits complement activation, wherein said protein consist of
   a) smallpox inhibitor of complement enzymes (SPICE) protein (SEQ ID NO:4),
   b) a fragment of SPICE, said fragment comprising at least a complement-inhibiting portion of SPICE, said portion including four short consensus repeats (SCRs) of SPICE, wherein said protein inhibits complement activation, and
   c) a SPICE-related fusion protein comprising at least one polypeptide moiety attached to at least a complement-inhibiting portion of SPICE protein (SEQ ID NO:4), said portion including four SCRs of SPICE.

15. The blood product of claim 14, comprising whole blood, packed red blood cells, fresh frozen plasma, plasma components, or purified antibodies.

16. A method of inhibiting complement activation in a human blood product, said method comprising the step of administering to said product a protein that inhibits complement activation, wherein the protein consist of
   a) smallpox inhibitor of complement enzymes (SPICE) protein (SEQ ID NO:4),
   b) a fragment of SPICE, said fragment comprising at least a complement-inhibiting portion of SPICE said portion including four short consensus repeats (SCRs) of SPICE, wherein said protein inhibits complement activation, and
   c) a SPICE-related fusion protein comprising at least one polypeptide moiety attached to at least a complement-inhibiting portion of SPICE protein (SEQ ID NO:4), said portion including four SCRs of SPICE.

* * * * *

SEQUENCE LISTING

```
<160> NUMBER OF SEQ ID NOS:  34

<210> SEQ ID NO 1
<211> LENGTH: 789
<212> TYPE: DNA
<213> ORGANISM: Vaccinia virus
<400> SEQUENCE: 1
atgaaggtgg agagcgtgac gttcctgaca ttgttgggaa taggatgcgt tctatcatgc     60
tgtactattc cgtcacgacc cattaatatg aaatttaaga atagtgtgga gactgatgct    120
aatgctaatt acaacatagg agacactata gaatatctat gtctacctgg atacagaaag    180
caaaaaatgg gacctatata tgctaaatgt acaggtactg gatggacact ctttaatcaa    240
tgtattaaac ggagatgccc atcgccacga gatatcgata atggccaact tgatattggt    300
ggagtagact ttggctctag tataacgtac tcttgtaata gcggatatca tttgatcggt    360
gaatctaaat cgtattgtga attaggatct actggatcta tggtatggaa tcccgaggca    420
cctatttgtg aatctgttaa atgccaatcc cctccatcta tatccaacgg aagacataac    480
ggatacgagg atttttatac cgatgggagc gttgtaactt atagttgcaa tagtggatat    540
tcgttgattg gtaactctgg tgtcctgtgt tcaggaggag aatggtccga tccacccacg    600
tgtcagattg ttaaatgtcc acatcctaca atatcaaacg gatacttgtc tagcgggttt    660
aaaagatcat actcatacaa cgacaatgta gactttaagt gcaagtacgg atataaacta    720
tctggttcct catcatctac ttgctctcca ggaaatacat ggaagccgga acttccaaaa    780
tgtgtacgc                                                            789

<210> SEQ ID NO 2
<211> LENGTH: 263
<212> TYPE: PRT
<213> ORGANISM: Vaccinia virus
<400> SEQUENCE: 2

Met Lys Val Glu Ser Val Thr Phe Leu Thr Leu Leu Gly Ile Gly Cys
  1               5                  10                  15

Val Leu Ser Cys Cys Thr Ile Pro Ser Arg Pro Ile Asn Met Lys Phe
             20                  25                  30

Lys Asn Ser Val Glu Thr Asp Ala Asn Ala Asn Tyr Asn Ile Gly Asp
         35                  40                  45

Thr Ile Glu Tyr Leu Cys Leu Pro Gly Tyr Arg Lys Gln Lys Met Gly
     50                  55                  60

Pro Ile Tyr Ala Lys Cys Thr Gly Thr Gly Trp Thr Leu Phe Asn Gln
 65                  70                  75                  80

Cys Ile Lys Arg Arg Cys Pro Ser Pro Arg Asp Ile Asp Asn Gly Gln
                 85                  90                  95

Leu Asp Ile Gly Gly Val Asp Phe Gly Ser Ser Ile Thr Tyr Ser Cys
            100                 105                 110

Asn Ser Gly Tyr His Leu Ile Gly Glu Ser Lys Ser Tyr Cys Glu Leu
        115                 120                 125

Gly Ser Thr Gly Ser Met Val Trp Asn Pro Glu Ala Pro Ile Cys Glu
    130                 135                 140

Ser Val Lys Cys Gln Ser Pro Pro Ser Ile Ser Asn Gly Arg His Asn
145                 150                 155                 160

Gly Tyr Glu Asp Phe Tyr Thr Asp Gly Ser Val Val Thr Tyr Ser Cys
```

-continued

```
                165                 170                 175

Asn Ser Gly Tyr Ser Leu Ile Gly Asn Ser Gly Val Leu Cys Ser Gly
            180                 185                 190

Gly Glu Trp Ser Asp Pro Pro Thr Cys Gln Ile Val Lys Cys Pro His
        195                 200                 205

Pro Thr Ile Ser Asn Gly Tyr Leu Ser Ser Gly Phe Lys Arg Ser Tyr
    210                 215                 220

Ser Tyr Asn Asp Asn Val Asp Phe Lys Cys Lys Tyr Gly Tyr Lys Leu
225                 230                 235                 240

Ser Gly Ser Ser Ser Ser Thr Cys Ser Pro Gly Asn Thr Trp Lys Pro
                245                 250                 255

Glu Leu Pro Lys Cys Val Arg
            260

<210> SEQ ID NO 3
<211> LENGTH: 789
<212> TYPE: DNA
<213> ORGANISM: Vaccinia virus

<400> SEQUENCE: 3
atgaaggtgg agagagtgac gttcctgaca ttgttgcgaa taggatgcgt tctatcatgc      60
tgtactattc cgtcacgacc cattaatatg aaatttaaga atagtgtgga gactgatgct     120
aatgctaatt acaacatagg agacactata gaatatctat gtctacctgg atacagaaag     180
caaaaaatgg gacctatata tgctaaatgt acaggtactg gatggacact ctttaatcaa     240
tgtattaaac ggagatgccc gtcgcctcga gatatcgata atggccatct tgatattggc     300
ggagtagact ttggctctag tataacgtac tcttgtaata gcggatatta tttgattggt     360
gaatataaat cgtattgtaa attaggatct actggatcta tggtatggaa tcccaaggca     420
cctatttgcg aatctgttaa atgccaatta cctccatcta tatccaacgg aagacataac     480
ggatataatg atttttatac cgatggaagc gttgtaactt atagttgcaa tagtggatat     540
tcgttgattg gtaactctgg tgtcctgtgt tcaggaggag aatggtctaa tccacccacg     600
tgtcagattg ttaaatgtcc acatcctaca atattaaacg gatacttgtc tagcgggttt     660
aaaagatcat attcgtataa tgacaatgta gactttacgt gcaagtacgg atataaacta     720
tctggttcct catcatctac ttgctctcca ggaaatacat ggcaaccgga acttccaaaa     780
tgtgtacgc                                                              789

<210> SEQ ID NO 4
<211> LENGTH: 263
<212> TYPE: PRT
<213> ORGANISM: Vaccinia virus

<400> SEQUENCE: 4

Met Lys Val Glu Arg Val Thr Phe Leu Thr Leu Leu Gly Ile Gly Cys
  1               5                  10                  15

Val Leu Ser Cys Cys Thr Ile Pro Ser Arg Pro Ile Asn Met Lys Phe
             20                  25                  30

Lys Asn Ser Val Glu Thr Asp Ala Asn Ala Asn Tyr Asn Ile Gly Asp
         35                  40                  45

Thr Ile Glu Tyr Leu Cys Leu Pro Gly Tyr Arg Lys Gln Lys Met Gly
     50                  55                  60

Pro Ile Tyr Ala Lys Cys Thr Gly Thr Gly Trp Thr Leu Phe Asn Gln
 65                  70                  75                  80
```

-continued

```
Cys Ile Lys Arg Arg Cys Pro Ser Pro Arg Asp Ile Asp Asn Gly His
                85                  90                  95

Leu Asp Ile Gly Gly Val Asp Phe Gly Ser Ser Ile Thr Tyr Ser Cys
            100                 105                 110

Asn Ser Gly Tyr Tyr Leu Ile Gly Glu Tyr Lys Ser Tyr Cys Lys Leu
        115                 120                 125

Gly Ser Thr Gly Ser Met Val Trp Asn Pro Lys Ala Pro Ile Cys Glu
    130                 135                 140

Ser Val Lys Cys Gln Leu Pro Pro Ser Ile Ser Asn Gly Arg His Asn
145                 150                 155                 160

Gly Tyr Asn Asp Phe Tyr Thr Asp Gly Ser Val Val Thr Tyr Ser Cys
                165                 170                 175

Asn Ser Gly Tyr Ser Leu Ile Gly Asn Ser Gly Val Leu Cys Ser Gly
            180                 185                 190

Gly Glu Trp Ser Asn Pro Pro Thr Cys Gln Ile Val Lys Cys Pro His
        195                 200                 205

Pro Thr Ile Leu Asn Gly Tyr Leu Ser Ser Gly Phe Lys Arg Ser Tyr
    210                 215                 220

Ser Tyr Asn Asp Asn Val Asp Phe Thr Cys Lys Tyr Gly Tyr Lys Leu
225                 230                 235                 240

Ser Gly Ser Ser Ser Ser Thr Cys Ser Pro Gly Asn Thr Trp Gln Pro
                245                 250                 255

Glu Leu Pro Lys Cys Val Arg
            260
```

<210> SEQ ID NO 5
<211> LENGTH: 789
<212> TYPE: DNA
<213> ORGANISM: Vaccinia virus

<400> SEQUENCE: 5

```
atgaaggtgg agagcgtgac gttcctgaca ttgttgggaa taggatgcgt tctatcatgc      60
tgtactattc cgtcacgacc cattaatatg aaatttaaga atagtgtgga gactgatgct     120
aatgctaatt acaacatagg agacactata gaatatctat gtctacctgg atacagaaag     180
caaaaaatgg gacctatata tgctaaatgt acaggtactg gatggacact ctttaatcaa     240
tgtattaaac ggagatgccc atcgccacga gatatcgata atggccatct tgatattggt     300
ggagtagact ttggctctag tataacgtac tcttgtaata gcggatatta tttgatcggt     360
gaatataaat cgtattgtaa attaggatct actggatcta tggtatggaa tcccaaggca     420
cctatttgtg aatctgttaa atgccaattg cctccatcta tatccaacgg aagacataac     480
ggatacaatg atttttatac cgatgggagc gttgtaactt atagttgcaa tagtggatat     540
tcgttgattg gtaactctgg tgtcctgtgt tcaggaggag aatggtccaa tccacccacg     600
tgtcagattg ttaaatgtcc acatcctaca atattaaacg gatacttgtc tagcgggttt     660
aaaagatcat actcatacaa cgacaatgta gactttacgt gcaagtacgg atataaacta     720
tctggttcct catcatctac ttgctctcca ggaaatacat ggcagccgga acttccaaaa     780
tgtgtacgc                                                             789
```

<210> SEQ ID NO 6
<211> LENGTH: 263
<212> TYPE: PRT
<213> ORGANISM: Vaccinia virus

<400> SEQUENCE: 6

```
Met Lys Val Glu Ser Val Thr Phe Leu Thr Leu Leu Gly Ile Gly Cys
 1               5                  10                  15

Val Leu Ser Cys Cys Thr Ile Pro Ser Arg Pro Ile Asn Met Lys Phe
            20                  25                  30

Lys Asn Ser Val Glu Thr Asp Ala Asn Ala Asn Tyr Asn Ile Gly Asp
            35                  40                  45

Thr Ile Glu Tyr Leu Cys Leu Pro Gly Tyr Arg Lys Gln Lys Met Gly
        50                  55                  60

Pro Ile Tyr Ala Lys Cys Thr Gly Thr Gly Trp Thr Leu Phe Asn Gln
65                  70                  75                  80

Cys Ile Lys Arg Arg Cys Pro Ser Pro Arg Asp Ile Asp Asn Gly His
                85                  90                  95

Leu Asp Ile Gly Gly Val Asp Phe Gly Ser Ser Ile Thr Tyr Ser Cys
                100                 105                 110

Asn Ser Gly Tyr Tyr Leu Ile Gly Glu Tyr Lys Ser Tyr Cys Lys Leu
            115                 120                 125

Gly Ser Thr Gly Ser Met Val Trp Asn Pro Lys Ala Pro Ile Cys Glu
130                 135                 140

Ser Val Lys Cys Gln Leu Pro Pro Ser Ile Ser Asn Gly Arg His Asn
145                 150                 155                 160

Gly Tyr Asn Asp Phe Tyr Thr Asp Gly Ser Val Val Thr Tyr Ser Cys
                165                 170                 175

Asn Ser Gly Tyr Ser Leu Ile Gly Asn Ser Gly Val Leu Cys Ser Gly
            180                 185                 190

Gly Glu Trp Ser Asn Pro Pro Thr Cys Gln Ile Val Lys Cys Pro His
        195                 200                 205

Pro Thr Ile Leu Asn Gly Tyr Leu Ser Ser Gly Phe Lys Arg Ser Tyr
210                 215                 220

Ser Tyr Asn Asp Asn Val Asp Phe Thr Cys Lys Tyr Gly Tyr Lys Leu
225                 230                 235                 240

Ser Gly Ser Ser Ser Ser Thr Cys Ser Pro Gly Asn Thr Trp Gln Pro
                245                 250                 255

Glu Leu Pro Lys Cys Val Arg
            260

<210> SEQ ID NO 7
<211> LENGTH: 26
<212> TYPE: DNA
<213> ORGANISM: Vaccinia virus

<400> SEQUENCE: 7
cgataatggc catcttgata ttggtg                                    26

<210> SEQ ID NO 8
<211> LENGTH: 27
<212> TYPE: DNA
<213> ORGANISM: Vaccinia virus

<400> SEQUENCE: 8
gctattaccg gtagaactat aaccacc                                   27

<210> SEQ ID NO 9
<211> LENGTH: 36
<212> TYPE: DNA
<213> ORGANISM: Vaccinia virus

<400> SEQUENCE: 9
```

```
cgtactcttg taatagcgga tattatttga tcgtg                              36

<210> SEQ ID NO 10
<211> LENGTH: 36
<212> TYPE: DNA
<213> ORGANISM: Vaccinia virus

<400> SEQUENCE: 10
gcatgagaac attatcgcct ataataaact agccac                             36

<210> SEQ ID NO 11
<211> LENGTH: 24
<212> TYPE: DNA
<213> ORGANISM: Vaccinia virus

<400> SEQUENCE: 11
gatcggtgaa tataaatcgt attg                                          24

<210> SEQ ID NO 12
<211> LENGTH: 24
<212> TYPE: DNA
<213> ORGANISM: Vaccinia virus

<400> SEQUENCE: 12
ctagccactt atatttagca taac                                          24

<210> SEQ ID NO 13
<211> LENGTH: 37
<212> TYPE: DNA
<213> ORGANISM: Vaccinia virus

<400> SEQUENCE: 13
aaatcgtatt gtaaattagg atctactgga tctatgg                            37

<210> SEQ ID NO 14
<211> LENGTH: 37
<212> TYPE: DNA
<213> ORGANISM: Vaccinia virus

<400> SEQUENCE: 14
tttagcataa catttaatcc tagatgacct agatacc                            37

<210> SEQ ID NO 15
<211> LENGTH: 29
<212> TYPE: DNA
<213> ORGANISM: Vaccinia virus

<400> SEQUENCE: 15
ggtatggaat cccaaggcac ctatttgtg                                     29

<210> SEQ ID NO 16
<211> LENGTH: 29
<212> TYPE: DNA
<213> ORGANISM: Vaccinia virus

<400> SEQUENCE: 16 ccataccttag ggttccgtg gataaacac                                     29

<210> SEQ ID NO 17
<211> LENGTH: 25
<212> TYPE: DNA
<213> ORGANISM: Vaccinia virus
```

-continued

```
<400> SEQUENCE: 17
ctgttaaatg ccaattgcct ccatc                                              25

<210> SEQ ID NO 18
<211> LENGTH: 25
<212> TYPE: DNA
<213> ORGANISM: Vaccinia virus

<400> SEQUENCE: 18
gacaatttac ggttaacgga ggtag                                              25

<210> SEQ ID NO 19
<211> LENGTH: 35
<212> TYPE: DNA
<213> ORGANISM: Vaccinia virus

<400> SEQUENCE: 19
gacataacgg atacaatgat ttttataccg atggg                                   35

<210> SEQ ID NO 20
<211> LENGTH: 35
<212> TYPE: DNA
<213> ORGANISM: Vaccinia virus

<400> SEQUENCE: 20
ctgtattgcc tatgttacta aaaatatggc taccc                                   35

<210> SEQ ID NO 21
<211> LENGTH: 25
<212> TYPE: DNA
<213> ORGANISM: Vaccinia virus

<400> SEQUENCE: 21
gaatggtcca atccacccac gtgtc                                              25

<210> SEQ ID NO 22
<211> LENGTH: 25
<212> TYPE: DNA
<213> ORGANISM: Vaccinia virus

<400> SEQUENCE: 22
cttaccaggt taggtgggtg cacag                                              25

<210> SEQ ID NO 23
<211> LENGTH: 41
<212> TYPE: DNA
<213> ORGANISM: Vaccinia virus

<400> SEQUENCE: 23
gtccacatcc tacaatatta aacggatact tgtctagggg g                            41

<210> SEQ ID NO 24
<211> LENGTH: 41
<212> TYPE: DNA
<213> ORGANISM: Vaccinia virus

<400> SEQUENCE: 24
caggtgtagg atgttataat ttgcctatga acagatcgcc c                            41

<210> SEQ ID NO 25
<211> LENGTH: 30
<212> TYPE: DNA
<213> ORGANISM: Vaccinia virus
```

```
<400> SEQUENCE: 25
cgacaatgta gactttacgt gcaagtacgg                                30

<210> SEQ ID NO 26
<211> LENGTH: 30
<212> TYPE: DNA
<213> ORGANISM: Vaccinia virus

<400> SEQUENCE: 26
gctgttacat ctgaaatgca cgttcatgcc                                30

<210> SEQ ID NO 27
<211> LENGTH: 25
<212> TYPE: DNA
<213> ORGANISM: Vaccinia virus

<400> SEQUENCE: 27
ggaaatacat ggcagccgga acttc                                     25

<210> SEQ ID NO 28
<211> LENGTH: 25
<212> TYPE: DNA
<213> ORGANISM: Vaccinia virus

<400> SEQUENCE: 28
cctttatgta ccgtcggcct tgaag                                     25

<210> SEQ ID NO 29
<211> LENGTH: 23
<212> TYPE: DNA
<213> ORGANISM: Vaccinia virus

<400> SEQUENCE: 29
aggaattccg ccgcgggggc ttc                                       23

<210> SEQ ID NO 30
<211> LENGTH: 21
<212> TYPE: DNA
<213> ORGANISM: Vaccinia virus

<400> SEQUENCE: 30
caatgtatta aacggagatg c                                         21

<210> SEQ ID NO 31
<211> LENGTH: 21
<212> TYPE: DNA
<213> ORGANISM: Vaccinia virus

<400> SEQUENCE: 31
tgttcaggag gagaatggtc c                                         21

<210> SEQ ID NO 32
<211> LENGTH: 21
<212> TYPE: DNA
<213> ORGANISM: Vaccinia virus

<400> SEQUENCE: 32
ggaccattct cctcctgaac a                                         21

<210> SEQ ID NO 33
<211> LENGTH: 21
<212> TYPE: DNA
```

```
<213> ORGANISM: Vaccinia virus

<400> SEQUENCE: 33
gcatctccgt ttaatacatt g                                      21

<210> SEQ ID NO 34
<211> LENGTH: 21
<212> TYPE: DNA
<213> ORGANISM: Vaccinia virus

<400> SEQUENCE: 34
ctgtaagtca cagacaatcc t                                      21
```